(12) United States Patent
Genard

(10) Patent No.: US 7,683,026 B2
(45) Date of Patent: Mar. 23, 2010

(54) METHOD FOR SYNTHESIZING KPV TRIPEPTIDE DIAMIDE DERIVATIVES

(75) Inventor: Sylvie Genard, Nogent sur Marne (FR)

(73) Assignee: L'Oreal (FR)

( * ) Notice: Subject to any disclaimer, the term of this patent is extended or adjusted under 35 U.S.C. 154(b) by 691 days.

(21) Appl. No.: 10/764,158

(22) Filed: Jan. 23, 2004

(65) Prior Publication Data

US 2004/0171797 A1  Sep. 2, 2004

Related U.S. Application Data

(60) Provisional application No. 60/507,998, filed on Oct. 2, 2003.

(30) Foreign Application Priority Data

Jan. 24, 2003  (FR) .................................. 03 00808

(51) Int. Cl.
*A61K 38/00* (2006.01)
*A61K 38/06* (2006.01)
*A61K 51/00* (2006.01)

(52) U.S. Cl. .......................... 514/2; 530/331; 424/1.69

(58) Field of Classification Search ...................... 514/2; 530/331
See application file for complete search history.

(56) References Cited

U.S. PATENT DOCUMENTS 5,028,592 A * 7/1991 Lipton .......................... 514/18
5,580,855 A * 12/1996 Ferreira et al. ................ 514/18
5,786,336 A * 7/1998 Kauvar et al. ................. 514/18

FOREIGN PATENT DOCUMENTS

WO  WO 88/00833  2/1988
WO  WO 02/069884  9/2002

OTHER PUBLICATIONS

Eberle, A. N. (ed) "The Melanotropins, chemistry...", Karger Press, 1988, pp. 336-337 and 346-348 (cited in Ferreira et al.).*
Database CA, Chemical Abstracts Service, Columbus, Ohio, US, Eberle, Alex et al., Hormone-receptor interactions. Syntheses of alpha-rnelanotropin . . . using alkali-labile protecting groups, retrieved from STN Database accession No. 84:59984 CA XP002263994 & Helvetica Chimica Acta (1975), 58(7), 2106-29 (cited in Applicant's IDS Jan. 23, 2004).*
Database CA, Chemical Abstracts Service, Columbus, Ohio, US, Eberle, Alex et al., "Hormone-receptor interactions. Syntheses of alpha-melanotropin and information-carrying sequences using alkali-labile protecting groups," retrieved from STN Database accession No. 84:59984 CA XP002263994 & Helvetica Chimica Acta (1975), 58(7), 2106-29.

* cited by examiner

*Primary Examiner*—Maury Audet
(74) *Attorney, Agent, or Firm*—Lerner, David, Littenberg, Krumholz & Mentlik, LLP

(57) ABSTRACT

The object of the invention is to provide an improved method for synthesizing a KPV tripeptide diamide derivate having the formula (I) such as defined in the specification. The synthesis method according can be implemented with any of the stereoisomers of each of the Lysine (K), Proline (P) or Valine (V) amino acid residues.

18 Claims, 6 Drawing Sheets

METHOD FOR SYNTHESIZING KPV TRIPEPTIDE DIAMIDE DERIVATIVES

CROSS-REFERENCE TO RELATED APPLICATIONS

The present application claims the benefit of French Application No. 0300808, filed Jan. 24, 2003, and U.S. Provisional Application No. 60/507,998, filed Oct. 2, 2003, the disclosures of which are incorporated by reference herein.

BACKGROUND OF THE INVENTION

The present invention relates to an improved method for synthesizing diamide derivates of the Lysine-Proline-Valine (KPV) tripeptide.

PRIOR ART

In peptide synthesis, two main synthesis routes are to be distinguished, i.e. solid phase synthesis and solution synthesis.

The solid phase synthesis has the advantage of a high flexibility and an already existing automation. The products are generally synthesized at laboratory scales ranging in most cases from a few milligrams to one hundred milligrams. Its principle is based on that of the support chemistry with its known advantages, in particular, in terms of purification allowing for the implementation of reagent excess for enhancing the yield. Such a route is generally used for synthesizing a large number of compounds with a view to screening their activity.

The solution synthesis has, as far as it is concerned, the advantage of making it possible to prepare large product amounts in one single batch. All the reactions are achieved in solution without using any reagent supported on a resin as in the previous case. In peptide synthesis, it is the most preferred method for an industrial synthesis.

Hemisynthesis reactions from natural peptides may be also mentioned. They consist in the limited hydrolysis (most often via enzymatic route) of natural occurring peptides leading to a blend of fragments of peptide nature which are separated and subsequently optionally derivatized to obtain the desired compounds.

SOLUTION SYNTHESIS

To the Applicant's knowledge, one single publication discloses the solution synthesis of diamide compounds of the KPV tripeptide, the only exemplified compound being Ac-Lys-Pro-Val-$NH_2$ (Eberle et al., 1975).

In such a synthesis, the lysine side chain is protected by a MSOC protective group introduced onto Boc-Lys-OH so as to form Boc-Lys(MSOC)-OH. The diprotected $N(\alpha),N(\epsilon)$ lysine is coupled with Boc-Pro-Val-$NH_2$, HCl by the conventional DCC/HOBt method. The Boc-Pro-Val-$NH_2$, HCl reactant is in turn obtained in two steps from Boc-Pro-OH and Boc-Val-$NH_2$. The overall yield is 33% calculated based on Boc-Lys(MSOC)-OH. The global synthesis scheme is illustrated in the scheme (I) hereunder:

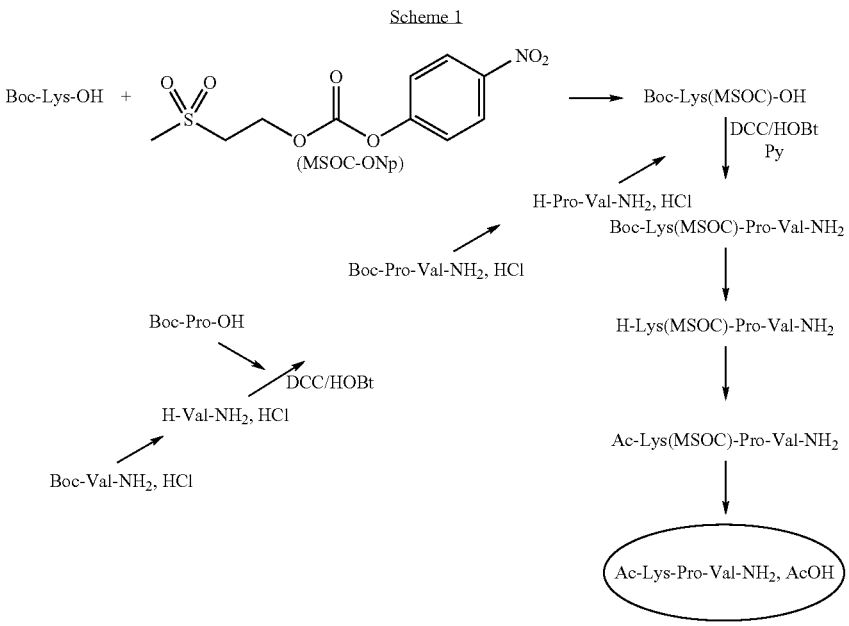

A rough and incomplete preparation of said Ac-Lys-Pro-Val-$NH_2$ compound (unspecified salt) and the diacetylated Ac-Lys(Ac)-Pro-Val-$NH_2$ homologue thereof is mentioned in European Patent Application N° EP-0,317,573 (Lipton).

In other documents, such as the International Application WO0056353 (Lipton), the Ac-Lys-Pro-Val-$NH_2$ compound is mentioned, but only an indication of the synthesis mode is given. It is stated that <<the peptides were prepared via a solid phase peptide synthesis and purified through reverse phase high performance liquid chromatography>>.

SOLID PHASE

In solid phase, the synthesis of Ac-LysPro-Val-NH2 is described in a L series with an overall yield of 56.1%.(Sawyer, 1981).

Still in solid phase, the article by Staples et al. (1985) discloses a peptide synthesis allowing to obtain the Ac-Lys-Pro-Val-NH$_2$ compound, but with some inconsistency between the structure and the amino acid analyses indicating the presence of Glycine. The solid phase methodology used by Sawyer in his thesis (Sawyer, 1981) is generalized to the synthesis of Ac-Peptide-NH$_2$ peptides (Sawyer, 1982) without the Ac-Lys-Pro-Val-NH$_2$ tripeptide being exemplified nor mentioned. In such a methodology (Sawyer, 1981; 1982), the resin is a p-methylbenzhydrylamine type resin allowing for the direct obtention with good yields of the carboxamide form (CO—NH$_2$) after cleavage of the resin peptide by hydrofluoric acid HF. The amino acids are introduced under their N-protected form by a Boc and are coupled by the conventional DCC/HOBt technique. In the case of lysine, it is introduced under a N($\alpha$)Boc, N($\alpha$)-2,4-Cl2-Z-Lys-OH form. When the peptide is synthesized, the protection of the N($\alpha$) amine of the last coupled amino acid is deprotected and the terminal amino acid is acetylated by an N-acetylimidazole excess before cleavage of the resin. Through such a methodology, the Ac-Lys-Pro-Val-NH2 tripeptide is synthesized with an overall yield of 56.1% (Sawyer, 1981) according to the scheme 2 hereinafter:

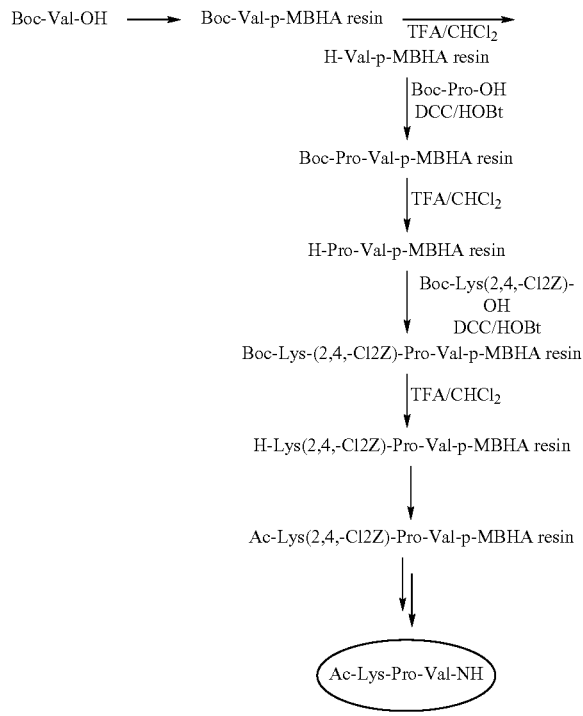

General Principle of the Syntheses Disclosed in the State of the Art

In the scheme 1, the key intermediate compound allowing to obtain KPV tripeptide diamides is Boc-Lys(MSOC)-Pro-Val-NH$_2$, both protective groups being released in different operating conditions. Through a specific release of the N($\alpha$) protective group of the (Boc) lysine, the free amine function is amidated and then the N($\epsilon$) amine function of the lysine is released in turn.

More generally, the synthesis of the type (I) derivates could be contemplated from intermediate compounds of the H-Lys-Pro-Val-OH (or the derivates thereof) tripeptide synthesis as long as both N($\alpha$) and N($\epsilon$) amine functions of the lysine are protected by labile protective groups in different operating conditions.

The tripeptide diprotected derivates are disclosed in the state of the art.

Thus, the U.S. Pat. No. 5,580,855 (Ferreira) discloses the solid phase synthesis of the H-Lys-Pro-Val-OH tripeptide using FMOC as a protective group of the $\alpha$ amine function and as a solid phase, a polymethacrylamide polymer synthesized from three different monomers. Introducing the amino acids occurs through their activation under a symmetrical anhydride form. In the case of lysine, the N($\epsilon$) amine function is protected by a Boc. At synthesis completion, the tripeptide is released from the solid support by using trifluoroacetic acid (deprotecting the Boc groups as well), the FMOC being preliminarily released by 20% piperidine in DMF.

Preparing the H-Lys(Boc)-Pro-Val-NH$_2$ intermediate compound (or the salts thereof) is disclosed in particular by Suli-Vargha et al. (1987), Suli-Vargha et al. (1984), Schwyzer et al. (1963) as well as in the European Patent Application published under n° EP 78167.

Amongst the other protected intermediate compounds are to be mentioned for example H-Lys(formyl)-Pro-Val-NH2, HCl prepared from Z-Lys(formyl)-Pro-Val-NH$_2$ (Suli-Vargha et al., 1987), or H-Lys(Z)-Pro-Val-NH$_2$ (or the salts thereof) (Yasutake and Powers, 1981) and H-Lys(Tosyl)-Pro-Val-NH$_2$ (Hofmann et al., 1960).

As previously set forth, the methods for synthesizing the KPV tripeptide diamide derivates in the state of the art have the following disadvantages:

(a) the solid phase synthesis methods allow to obtain KPV peptide diamide derivates with a satisfactory purity degree but are only adapted for producing small amounts of final products, from a few milligrams to a few hundreds milligrams, incompatible with industrial needs;

(b) the solution synthesis methods allow to prepare large amounts of the final product, but with an unsatisfactory yield, in the order of 33%. Such solution synthesis methods require subsequent long and expensive purification steps of the final product, and lead to a significant quantitative loss of the product, when going from the non purified form to the purified form.

There is consequently a need in the state of the art for a method for synthesizing KPV tripeptide diamide derivates in order to directly obtain large amounts of the final product, with a high yield, and without requiring any specific purification step.

SUMMARY OF THE INVENTION

Such a method for synthesizing a KPV tripeptide diamide derivate is provided according to the invention. The synthesis method according to the invention may be achieved with any one of the stereoisomers in each of the Lysine (K), Proline (P) or Valine (V) amino acid residues.

The object of the invention is to provide a solution synthesis method for a KPV tripeptide diamide derivate represented by formula (I), or also for a derivate salt having the following formula (I):

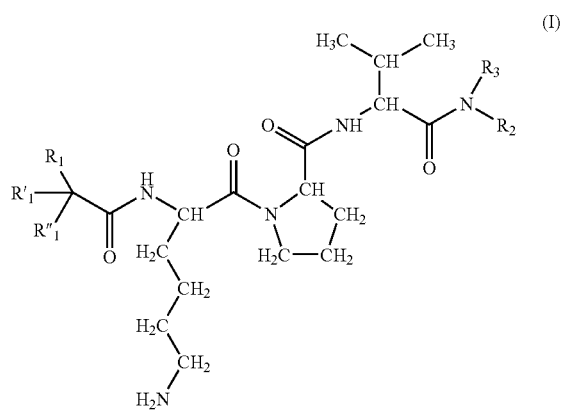

(I)

independently from the stereochemistry of the implemented amino acids wherein:

a) $R_1$, $R'_1$ and $R''_1$ represent, independently from each other, a hydrogen atom or a linear or branched $C_1$-$C_{22}$ alkyl moiety, optionally interrupted by a heteroatom such as O or N or S or Si, $C_4$-$C_{10}$ cycloalkyl moiety, a linear or branched $C_1$-$C_{22}$ polyfluoroalkyl or perfluoroalkyl moiety, an aryl moiety optionally substituted by one or more halogen atoms such as Cl, F, Br or I or one or more linear or branched $C_1$-$C_4$ alkyl moieties, an aralkyl moiety, or $R_1$ and $R'_1$ could form with $C(R''_1)$ a saturated ring with from 3 to 7 atoms, optionally substituted by one or more linear or branched $C_1$-$C_4$ alkyl moieties and/or optionally containing a heteroatom such as O, S or N, with the proviso that the $R_1(R'_1)(R''_1)CO$ group does not represent an amino acid residue or a peptide residue;

b) $R_2$ and $R_3$ represent, independently from each other, a hydrogen atom or represent a linear or branched $C_1$-$C_{24}$ alkyl moiety, optionally interrupted by a heteroatom such as O or N or S or Si, a $C_4$-$C_{10}$ cycloalkyl moiety, a linear or branched $C_1$-$C_{22}$ polyfluoroalkyl or perfluoroalkyl moiety, an aryl moiety optionally substituted by one or more halogen atoms such as Cl, F, Br or I, or one or more linear or branched $C_1$-$C_4$ alkyl moieties, an aralkyl moiety, or $R_2$ and $R_3$ could form with the nitrogen atom a saturated ring with from 5 or 6 atoms optionally substituted by one or more linear or branched $C_1$-$C_4$ alkyl moieties, said saturated ring optionally containing a heteroatom such as O, S or also an additional nitrogen atom, with the proviso that the $N(R_2)(R_3)$ group does not represent an amino acid or a peptide residue;

said method being characterized in that it comprises the following steps of:

a) reacting a lysine diprotected residue having the following formula (II):

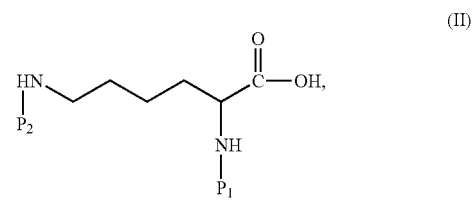

(II)

optionally salified by a mineral or organic base, wherein $P_1$ and $P_2$, different from one another, each represent independently from one another a protective group, with a Proline residue having the following formula (III):

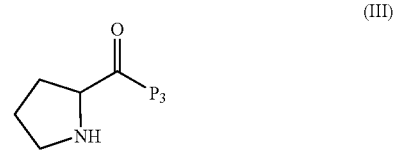

(III)

optionally salified by a mineral or organic acid, wherein $P_3$ represents a protective group differing from any of the $P_1$ and $P_2$ protective groups, or wherein $P_3$ represents a hydroxyl group, in the presence of an activation reagent or a coupling reagent in a solvent, so as to obtain the following compound having the formula (IV):

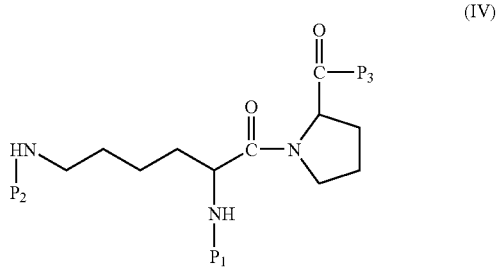

(IV)

wherein $P_1$, $P_2$ and $P_3$ have the above-mentioned meanings.

b)

1) coupling, on the C-terminal function of the Proline residue of the compound with formula (IV) wherein $P_3$ represents OH, a valine compound having the following formula (V):

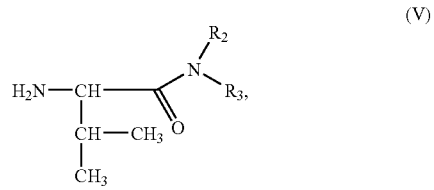

(V)

wherein $R_2$ and $R_3$ have the same meaning as hereinabove, and removing the $P_1$ protective group, 2) amidating the NH$_2$(α) group in a N-terminal position of the lysine residue by a compound having the following formula (VI-A) or (VI-B):

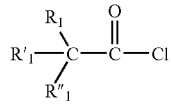

(VI-A)

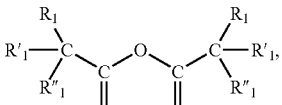

(VI-B)

so as to obtain the following compound having the formula (XII):

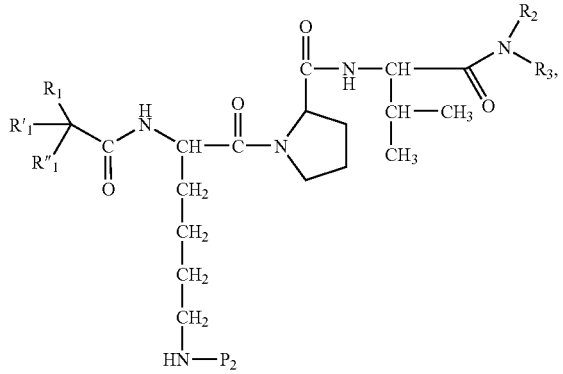

(XII)

wherein P$_2$, R$_1$, R'$_1$, R"$_1$, R$_2$ and R$_3$ have the same meaning as hereinabove;

the order for the steps 1) and 2) being indifferent;

c) removing the P$_2$ protective group from the compound having the formula (XII) so as to obtain the compound having the formula (I), optionally under the form of a mineral or organic salt.

In formula (I), the R$_1$, R'$_1$ and R"$_1$ substituents are identical or different. They could have the following values:

hydrogen a linear or branched C$_1$-C$_{22}$ alkyl moiety, optionally interrupted by a heteroatom such as O or N or S or Si, a C$_4$-C$_{10}$ cycloalkyl moiety, a linear or branched C$_1$-C$_{22}$ polyfluoroalkyl or perfluoroalkyl moiety, an aryl optionally substituted by one or more halogen atoms such as Cl, F, Br or I, or one or more linear or branched C$_1$-C$_4$ alkyl groups, an aralkyl moiety, R$_1$ and R'$_1$ could form with C(R"$_1$) a saturated ring with from 3 to 7 atoms, optionally substituted by one or more linear or branched C$_1$-C$_4$ alkyl moieties and/or optionally containing a heteroatom such as O, S or N.

On the contrary, the R$_1$(R'$_1$)(R"$_1$)CO group should not represent an amino acid residue or a peptide chain.

In formula (I), the R$_2$ and R$_3$ substituents are identical or different. They could have the following values:

hydrogen a linear or branched C$_1$-C$_{24}$ alkyl moiety, optionally interrupted by a heteroatom such as O or N or S or Si, a C$_4$-C$_{10}$ cycloalkyl moiety, a linear or branched C$_1$-C$_{22}$ polyfluoroalkyl or perfluoroalkyl moiety, an aryl optionally substituted by one or more halogen atoms such as Cl, F, Br or I, or one or more linear or branched C$_1$-C$_4$ alkyl groups, an aralkyl moiety, R$_2$ and R$_3$ could form with the nitrogen atom a saturated ring with 5 or 6 atoms, optionally substituted by one or more linear or branched C$_1$-C$_4$ alkyl moieties, said saturated ring optionally containing a heteroatom such as O, S or as well an additional nitrogen atom.

On the contrary, the N(R$_2$)(R$_3$) group should not represent an amino acid or a peptide chain.

The term <<alkyl>> means a linear or branched aliphatic hydrocarbon group, optionally interrupted by one heteroatom, the alkyl group being either not substituted or substituted on the carbon atoms by one or more identical or different substituents, the substituents being selected amongst aryl, hydroxy, alkoxy, aryloxy, alkyloxy, aralkyloxy moieties. The term <<branched>> alkyl means a lower alkyl such as a methyl, ethyl or propyl group which is linked with an alkyl linear chain. The preferred alkyl groups comprise the <<lower alkyl>> groups having from 1 to 8 carbon atoms. Examples of alkyl groups are methyl, ethyl, i-propyl, t-butyl, heptyl, decyl or cyclohexylmethyl groups.

The term <<cycloalkyl>> means a non aromatic ring comprising from 4 to 10 carbon atoms, the cyclic alkyl group being optionally partly unsaturated. Preferred cycloalkyls comprise cyclopentyl, cyclohexyl, cycloheptyl, adamantyl, octahydronaphthyl and perhydronaphthyl groups.

The term <<aryl>> means an aromatic carbocyclic moiety containing from 5 to 10 carbon atoms. Aryl groups comprise unsubstituted phenyl or naphthyl or phenyl or naphthyl substituted by one or more substituents which may be identical or different, including alkyl, aryl, aralkyl, hydroxy, alkoxy, aryloxy, aralkoxy, carboxy, aroyl, halo, nitro, trihalomethyl, cyano, alkoxycarbonyl, aryloxycarbonyl, aralkoxycarbonyl, carbamoyl, alkylcarbamoyl, dialkylcarbamoyl substituents.

The term <<alkoxy>> means an alkyl-O— group wherein the alkyl group is as previously defined. The alkoxy groups include methoxy, ethoxy, n-propoxy, i-propoxy, n-butoxy and heptoxy groups.

The term <<aryloxy>> means an aryl-O group where the aryl group is such as previously defined. The aryloxy groups include phenoxy and naphthoxy groups.

The term <<aralkyl>> means an alkyl group substituted by one or more aryl groups.

The term <<aralkyloxy>> means an aralkyl-O— group where the aralkyl group is such as previously defined. The aralkyloxy groups include benzyloxy groups.

The term <<alkoxycarbonyl>> means a —O—CO— group, such as methoxy- and ethoxycarbonyl groups.

The term <<aryloxycarbonyl>> means an aryl-O—CO— group, such as phenoxy- and naphthoxycarbonyl groups.

The term <<halo>> means a fluorine, chlorine or bromine atom.

The method according to the invention more particularly makes possible to obtain those derivates under a salified form. The salts of compounds according to the invention are selected amongst the salts of a mineral or organic acid such as for example hydrochlorides, hydrobromides, sulphate, acetate, citrate, tartrate, lactate, phosphate, hydrogenophosphate, propionate or succinate.

The method according to the invention additionally has the advantage of being applicable on an industrial scale, for producing batches of KPV tripeptide diamide derivates weighing several kilograms and this, whatever the stereochemistry of the implemented amino acids is.

The invention also relates to the above defined KPV tripeptide diamide derivates represented by formula (I) with the additional proviso that $R_1$, $R'_1$, $R''_1$, $R_2$ and $R_3$ do not simultaneously represent a hydrogen atom (formula IA).

Such derivates may be present as salts, more particularly those previously mentioned.

DETAILED DESCRIPTION

Figure 1A:
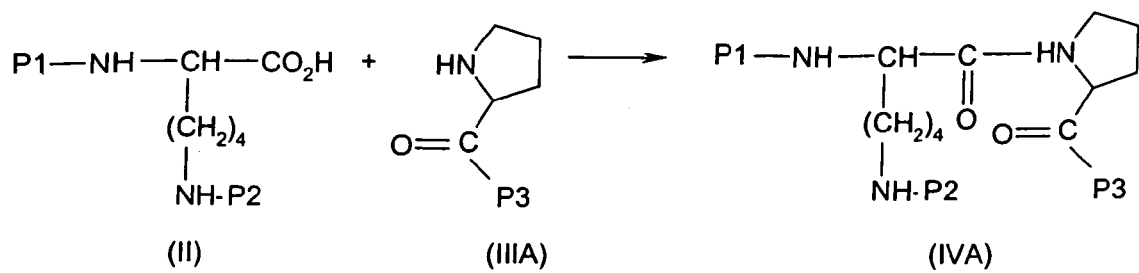
FIG. 1A illustrates an embodiment of the coupling method between the lysine residue and the proline residue, where the carboxyl function of the proline residue is protected by a $P_3$ protective group.

It is shown, according to the invention, that a particular combination of synthesis steps and the use of a particular combination of protective groups make it possible to prepare KPV tripeptide diamide derivates, or a salt of such compounds, in a solution synthesis method with a final yield much higher than the yield obtained with the known state of the art methods, and such a method does not require any final purification step, such as for example via ion exchange chromatography.

It has been shown that an appropriate selection of the protective groups, the reagents to be used and the reaction sequence makes it possible to increase the yield, in a solution synthesis, from 33% (Eberle et al., 1975) to more than 70% in the case of Ac-Lys-Pro-Val-$NH_2$.

The reagent/protective group combinations and the reaction step sequence are novel for the preparation of compounds of the formula (I).

Additionally, the synthesis method of the invention is applicable on an industrial scale. Isolating the final product is straightforward and does not require any chromatography purification or ion exchange column purification. Such tedious techniques are not implemented at any stage of the synthesis. At the completion of step c) of the method according to the invention, the KPV tripeptide diamide derivate is obtained directly with a very high purity. At the end of the synthesis, the purity of the isolated, crystallized product could be higher than 95%, as this has been determined by high performance liquid chromatography (HPLC).

On the other hand, if the compound (I) is to be obtained under a salified form, said salification occurs in situ during the last step of the method, comprising removing the $P_2$ protective group, and does not require any additional step or any particular implementation.

An object of the invention is a solution synthesis method of a KPV tripeptide diamide derivate having formula (I), or also of a salt of a derivate having the following formula (I):

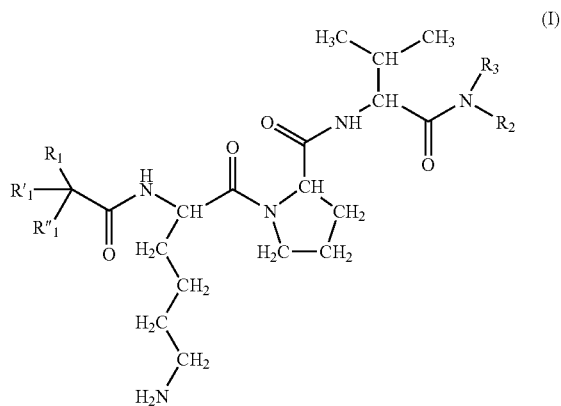

independently from the stereochemistry of the implemented amino acids wherein:

a) $R_1$, $R'_1$ and $R''_1$ represent, independently from each other, a hydrogen atom or
   a linear or branched $C_1$-$C_{22}$ alkyl moiety, optionally interrupted by a heteroatom such as O or N or S or Si,
   $C_4$-$C_{10}$ cycloalkyl moiety,
   a linear or branched $C_1$-$C_{22}$ polyfluoroalkyl or perfluoroalkyl moiety,
   an aryl moiety optionally substituted by one or more halogen atoms such as Cl, F, Br or I or one or more linear or branched $C_1$-$C_4$ alkyl moieties,
   an aralkyl moiety,
   or $R_1$ and $R'_1$ could form with $C(R''_1)$ a saturated ring with from 3 to 7 atoms, optionally substituted by one or more linear or branched $C_1$-$C_4$ alkyl moieties and/or optionally containing a heteroatom such as O, S or N, with the proviso that the $R_1(R'_1)(R''_1)CO$ group does not represent an amino acid residue or a peptide residue;

b) $R_2$ and $R_3$ represent, independently from each other, a hydrogen atom or represent
   a linear or branched $C_1$-$C_{2-4}$ alkyl moiety, optionally interrupted by a heteroatom such as O or N or S or Si,
   a $C_4$-$C_{10}$ cycloalkyl moiety,
   a linear or branched $C_1$-$C_{22}$ polyfluoroalkyl or perfluoroalkyl moiety,
   an aryl moiety optionally substituted by one or more halogen atoms such as Cl, F, Br or I, or one or more linear or branched $C_1$-$C_4$ alkyl moieties,
   an aralkyl moiety,
   or $R_2$ and $R_3$ could form with the nitrogen atom a saturated ring with from 5 or 6 atoms optionally substituted by one or more linear or branched $C_1$-$C_4$ alkyl moieties, said saturated ring optionally containing a heteroatom such as O, S or also an additional nitrogen atom, with the proviso that the $N(R_2)(R_3)$ group does not represent an amino acid or a peptide residue;

said method being characterized in that it comprises the following steps of:

a) reacting a lysine diprotected residue having the following formula (II):

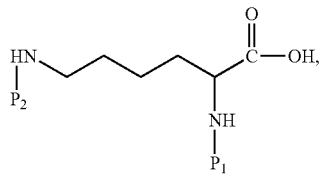

optionally salified by a mineral or organic base, wherein $P_1$ and $P_2$, different from one another, each represent independently from one another a protective group, with a Proline residue having the following formula (III):

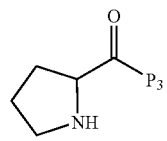

optionally salified by a mineral or organic acid, wherein $P_3$ represents a protective group differing from any of the $P_1$ and $P_2$ protective groups, or wherein $P_3$ represents a hydroxyl group, in the presence of an activation reagent or a coupling reagent in a solvent, so as to obtain the following compound having the formula (IV):

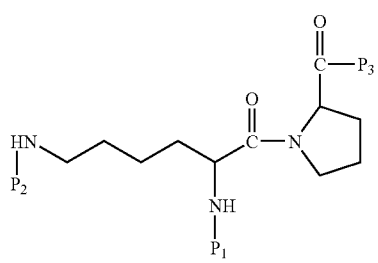

wherein $P_1$, $P_2$ and $P_3$ have the above-mentioned meanings.
b)
1) coupling, on the C-terminal function of the Proline residue of the compound with formula (IV) wherein $P_3$ represents OH, a valine compound having the following formula (V):

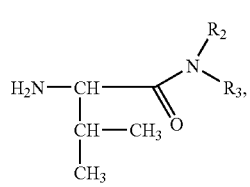

wherein $R_2$ and $R_3$ have the same meaning as hereinabove, and removing the A protective group, 2) amidating the $NH_2(\alpha)$ group in a N-terminal position of the lysine residue by a compound having the following formula (VI-A) or (VI-B):

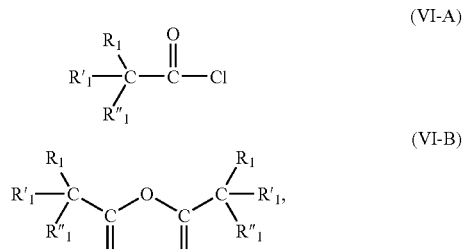

so as to obtain the following compound having the formula (XII):

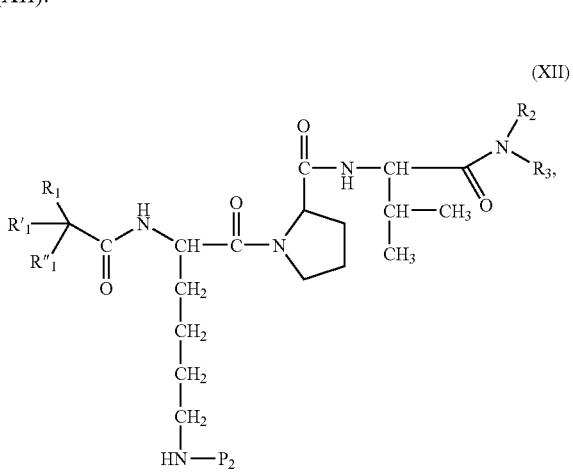

wherein $P_2$, $R_1$, $R'_1$, $R''_1$, $R_2$ and $R_3$ have the same meaning as hereinabove; the order for the steps 1) and 2) being indifferent;

c) removing the $P_2$ protective group from the compound having the formula (XII) so as to obtain the compound having the formula (I), optionally under the form of a mineral or organic salt.

At step c), removing the $P_2$ protective group is performed via hydrogenolysis. When the hydrogenolysis is performed with an acid contained in the reaction medium, said acid acts as a mineralizing agent of the amine function of the thereby released lysine. The final salt is preferably selected amongst hydrochlorides, hydrobromides, sulphates, acetates, citrates, tartrates, lactates, phosphates, hydrogenophosphates, propionates and succinates.

According to the invention, the method such as hereinabove defined could be implemented with any one of the stereoisomers of each of the Lysine, Proline or Valine amino acid residues.

Preferably, according to the method of the invention, the salt is obtained during step c) through introducing the corresponding acid.

Preferably, the acid to be used is selected amongst acetic acid, hydrochloric acid, hydrobromic acid, sulphuric acid, citric acid, tartaric acid, lactic acid, phosphoric acid, hydrogenophosphoric acid, propionic acid or succinic acid.

Most preferably, the acid is acetic acid or hydrochloric acid.

According to a preferred embodiment, the method of the invention is further characterized in that the $P_1$ et $P_2$ protective groups represent, independently from each other, Adoc (=1-adamantyloxycarbonyl), BOC (=t-butyloxycarbonyl), 2-bromo-Z (=2-bromo-benzyloxycarbonyl), or 2-chloro-Z (=2-chloro-benzyloxycarbonyl) or Fmoc (=9-fluorenyl-methoxycarbonyl) or Formyl or Nicotinoyl or 4-nitro-Z (mitro-benzyloxycarbonyl) or Tfa (=trifluoroacetyl) or Tos (=p-toluenesulfonyl) or Z(=benzyloxycarbonyl) or adpoc (=1-(adamantyl)-1-methylethoxy-carbonyl).

For preparing the compounds of the formula (I) in solution and/or the salts thereof, several synthesis routes can be contemplated, depending on whether the peptide part is built from the N-terminal end toward the C-terminal end or, inversely, from the C-terminal end toward the N-terminal end. Preferably, the peptide chain is built from the N-terminal end toward the C-terminal end.

The starting product of the synthesis method is lysine diprotected by 2 labile protective groups in different operating conditions in structure:

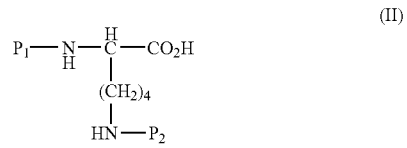

(II)

wherein $P_1$ and $P_2$ are different and could represent the following protective groups, with the proviso that $P_1$ be different from $P_2$ and that $P_1$ and $P_2$ be labile in distinct operating conditions: $P_1$, $P_2$=Adoc=(1-adamantyloxycarbonyl, Boc (=t-butyloxycarbonyl), 2-bromo-Z (=2-bromo-benzyloxycarbonyl), or 2-chloro-Z (=2-chloro-benzyloxycarbonyl) or Fmoc (=9-fluorenylmethoxycarbonyl) or Formyl or Nicotinoyl or 4-nitro-Z (=4-nitro-benzyloxycarbonyl) or Tfa (=trifluoroacetyl) or Tos (=p-toluenesulfonyl) or Z (=benzyloxycarbonyl) or Adpoc (=1-(1-adamantyl)-1-methylethoxycarbonyl), this non exhaustive list being only given by way of an example.

Most preferably, the $P_1$ and $P_2$ protective groups are selected so as to be removed respectively in distinct operating conditions.

The compound of the formula (II) could, in some cases, be salified by a base, preferably an organic base, and much more preferably, an organic amine such as for example dicyclohexylamine or ethyldiisopropylamine. Preferably, the compound with structure (II) is Boc-Lys (Z)-OH($P_1$ and $P_2$ respectively having the Boc and Z values).

The peptide coupling allowing for the introduction of the second amino acid occurs either with a C-protected derivate of the proline having structure (IIIA) (FIG. 1A) or with the proline having structure (IIIB) (FIG. 1B), the compounds (IIIA) and (IIIB) being both compounds with formula (III):

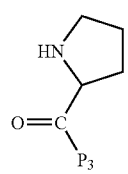

(IIIA)

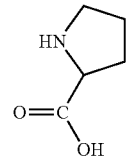

(IIIB)

The compounds with formula (III) are optionally salified by a mineral or organic acid. The compounds of the formula (III) are selected amongst H-Pro-AMC, H-Pro-p-nitrobenzylester, H-Pro-OtBu, H-Pro-OBzl, H-Pro-OMe, H-Pro-OEt preferably H-Pro-OBzl or H-Pro-OMe or H-Pro-OEt.

The peptide coupling of the diprotected lysine (II) with the C-protected proline (III) occurs by means of classical activating or coupling reagents in peptide synthesis such as carbodiimides such as DCC (=dicyclohexylcarbodiimide) or the water-soluble forms of carbodiimides such as EDC (=N-ethyl-N'-(3-dimethylaminopropyl)carbodiimide hydrochloride), phosphonium salts such as BOP (=benzotriazol-1-yloxy) tris(dimethylamino)phosphonium hexafluorophosphate), PyBOP (=(benzotriazol-1-yloxy) tripyrrolidinophosphonium hexafluorophosphate), PyBROP (=bromotripyrrolidinophosphonium hexafluorophosphate), PyCloP (=chlorotripyrrolidinophosphonium hexafluorophosphate), or also by means of reagents such as PyClU (=chloro-N,N,N',N'-bis(tetramethylene) formamidinium hexafluorophosphate), N-hydroxy-succinimide, EEDQ (=1-ethoxycarbonyl-2-ethoxy-1,2-dihydroquinolin), CDI (=carbonyldiimidazole), or also chloroformates such as ethyl chloroformate or isobutyl chloroformate. When coupling occurs by means of coupling reagents such as carbodiimides, additives such as HOBt (=1-hydroxybenzotriazole) or N-hydroxysuccinimide could be added during the reaction in order to limit racemization.

Preferably, according to the scheme in FIG. 1A, the peptide coupling occurs by means of carbodiimides, whether added or not with 1-hydroxybenzotriazole.

Figure 1B:
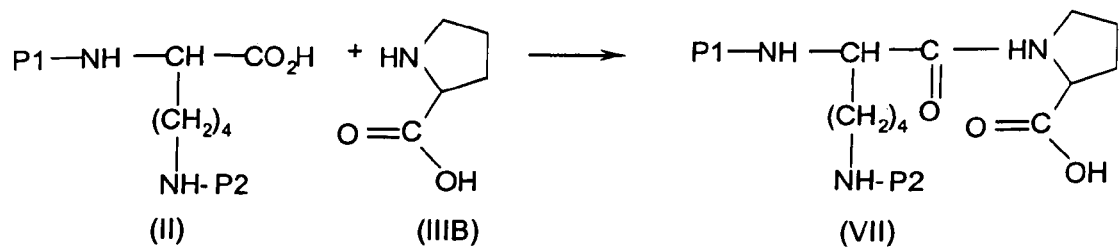
FIG. 1B illustrates an embodiment of the coupling method between the lysine residue and the praline residue, where the carboxyl function of the proline residue is free ($P_3$=OH).

Preferably, according to the scheme in FIG. 1B, coupling occurs with N-hydroxysuccinimide. In both cases, the preferred solvents are aprotic dipolar solvents, preferably dimethylformamide (DMF), N-methylpyrrolidone (NMP), or aprotic solvents such as 1,2-dimethoxyethane (DME), tetrahydrofurane (THF), dioxane, either pure or in blend.

The last peptide coupling occurs with C-amidated valine (V) optionally salified by a mineral or organic acid ($R_2$ and $R_3$ having the values as already defined), such an intermediate compound (V) being in turn prepared from BOC-Val-OH by amide synthesis methods from carboxylic acids.

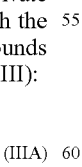 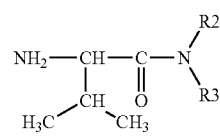

(V)

Figure 2:
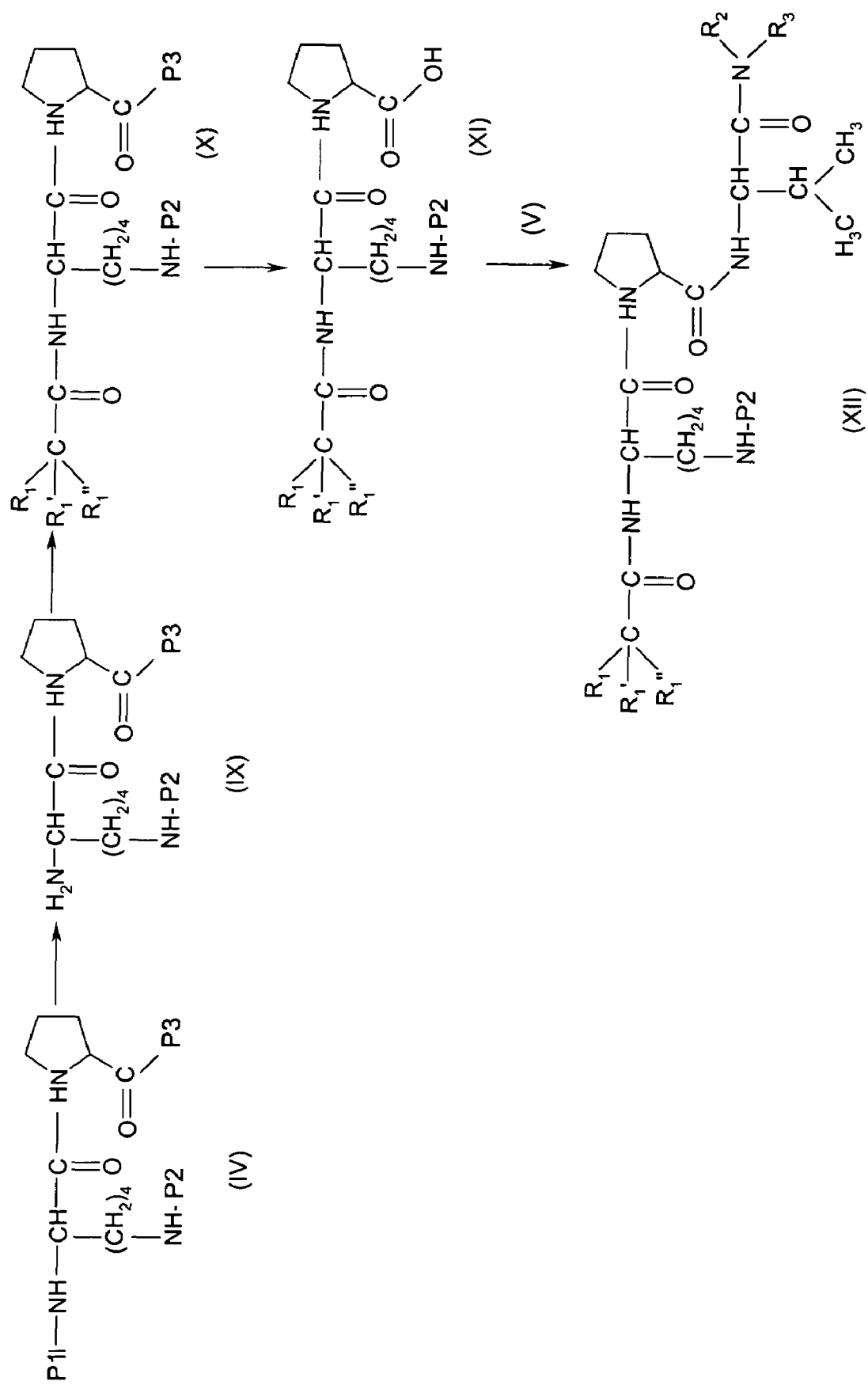
FIG. 2 illustrates the first preferred embodiment of the step b) of the method according to the invention.
Figure 3:
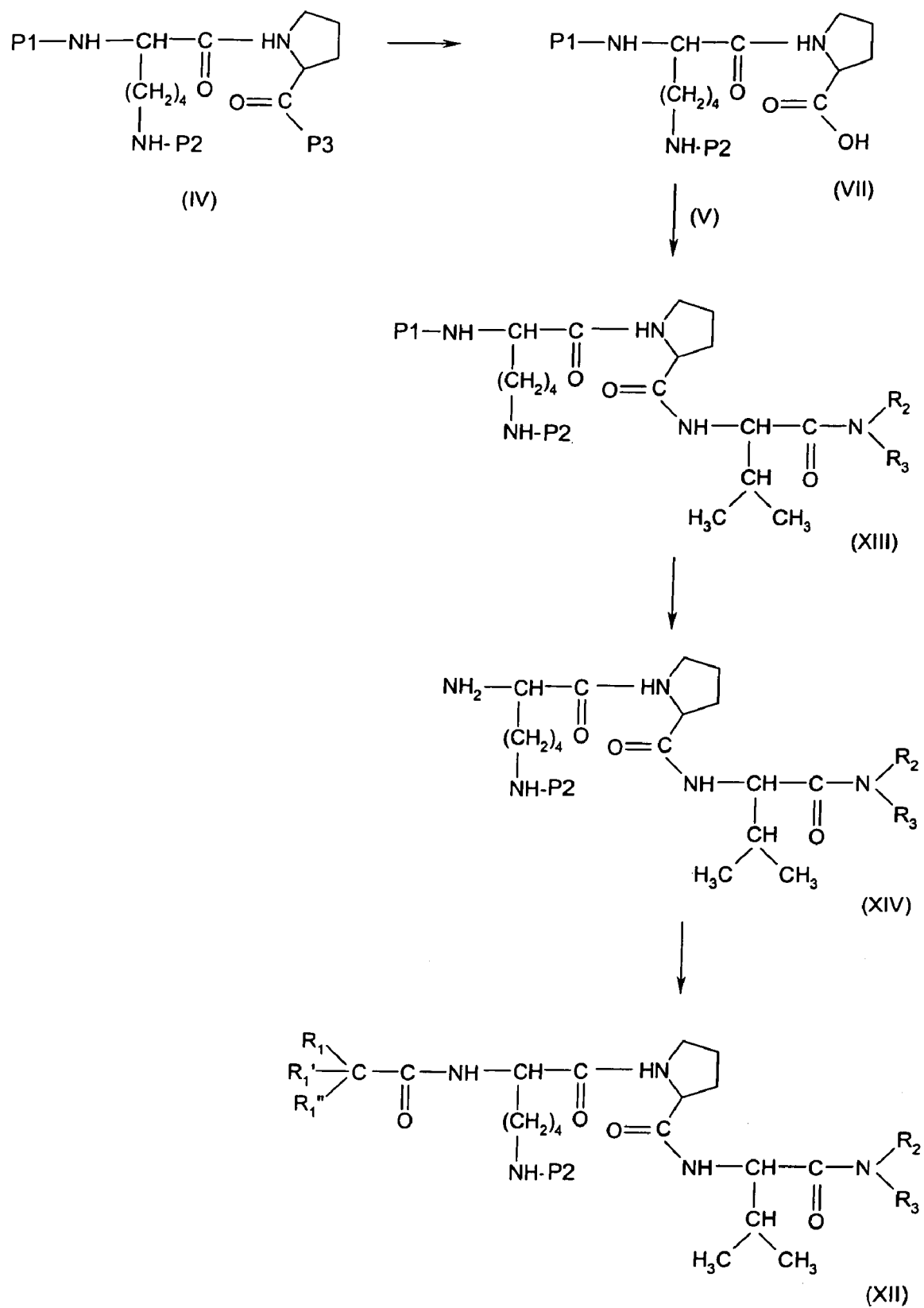
FIG. 3 illustrates the second preferred embodiment of the step b) of the method according to the invention.

Thus, the intermediate compound (IV) can be coupled with the intermediate compound (V) according to the scheme in FIG. 2 or the scheme in FIG. 3.

Similarly, the intermediate compound (VII) can be coupled with (V) according to the scheme in FIG. 3, the compound (VII) having the following formula:

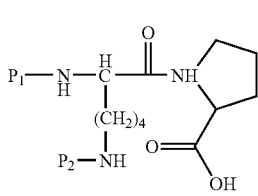
(VII)

First Preferred Embodiment of Step b) of the Method
(FIG. 2)

According to this first preferred embodiment of the synthesis method for the KPV tripeptide diamide derivates, the KP dipeptide (IV) has a proline residue the carboxylic group of which is protected by a P3 protective group and the coupling of the KP dipeptide (IV) with a valine derivate (IIIA) occurs after removal of the P1 protective group followed by the amidation of the thus released NH2($\alpha$) free amine function of the lysine residue. This first preferred embodiment is illustrated in FIG. 2.

According to such preferred embodiment, the method for synthesizing KPV tripeptide diamide derivates, such as defined hereinabove, is characterized in that the step b) comprises the following steps of:

b1) removing the $P_1$ protective group of the compound with formula (IV) wherein $P_3$ represents a protective group, so as to obtain the compound with formula (IX):

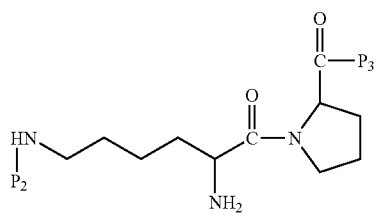
(IX)

wherein $P_1$ has the same meaning as hereinabove and $P_3$ represents a protective group;

b2) amidating the $NH_2(\alpha)$ group of the lysine residue of the compound of the formula (IX) with the following compound having the formula (VI-A) or the compound having the formula (VI-B):

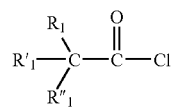
(VI-A)

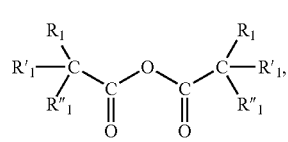
(VI-B)

wherein $R_1$, $R'_1$ and $R''_1$ have the same meanings as hereinabove so as to obtain the following compound with formula (X):

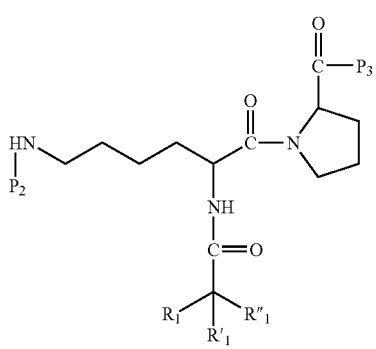
(X)

wherein $R_1$, $R'_1$, $R''_1$, $P_1$ have the same meaning as hereinabove and P3 represents a protective group;

b3) removing the $P_3$ protective group from the compound having formula (X) so as to obtain the compound with formula (XI):

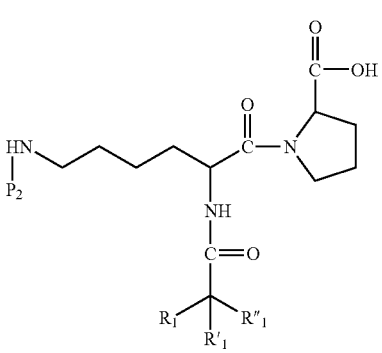
(XI)

wherein $R_1$, $R'_1$, $R''_1$ and $P_2$ have the same meaning as hereinabove;

b4) coupling the compound having formula (XI) with the valine compound having the following formula (V), optionally salified by a mineral or organic acid:

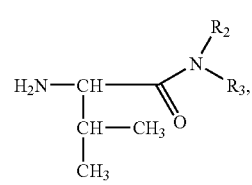
(V)

wherein $R_2$ and $R_3$ have the same meaning as hereinabove, so as to obtain the following compound having formula (XII):

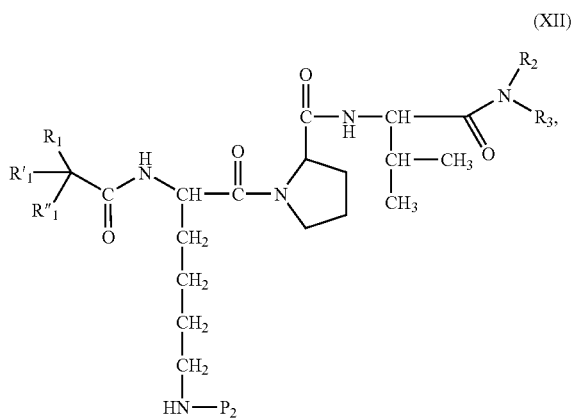

(XII)

wherein $P_2$, $R_1$, $R'_1$, $R''_1$, $R_2$ and $R_3$ have the same meanings as hereinabove.

According to the method illustrated in FIG. 2, the N(α) amine function of the lysine is released in the required conditions such as determined by the nature of the $P_1$ protective group being used. For example, if $P_1$ represents the BOC(=t-butyloxycarbonyl) group, the N(α) amine function of the lysine can be released by treating the corresponding compound (IV) with a mineral acid such as aqueous hydrochloric acid in an aprotic solvent such as dioxane or THF or also in a blend of solvents such as THF-$CH_2Cl_2$ or dioxane-$CH_2Cl_2$. The reaction then occurs between –10° C. and 40° C., preferably between 4° C. and 30° C. The N(α) amine function of the lysine of the compound (IX) is then amidated under the usual conditions such as for example through reaction with an acid chloride with structure (VI-A), or a symmetrical anhydride with structure (VI-B), or a dissymmetric anhydride, such a list being not exhaustive.

Preferably, the reaction occurs with an acid chloride (VI-A) or an anhydride (VI-B). The solvent is preferably an aprotic dipolar solvent such as DMF or NMP, or an aprotic solvent such as THF, dioxane, those solvents being used either pure or in a blend, or a blend of solvents such as $CH_2Cl_2$/water for example.

If the compound (IX) is under a salified form, the reaction medium is added with a sufficient amount of an organic base such as triethylamine, ethyldiisopropylamine, butylamine for example, or a mineral base such as NaOH, KOH, $Na_2CO_3$, $K_2CO_3$, $KHCO_3$, $NaHCO_3$ for example.

The C-terminal acid function of the thus obtained compound (X) is then released in the required operating conditions such as determined by the nature of the $P_3$ protective group. For example, if $P_3$ represents the OBzl benzyl ester, the acid function can be released adding to the compound (X) a mineral or an organic base, preferably a mineral base such as NaOH for example. In the latter case, such a deprotection occurs in an alcohol medium such as ethanol or methanol or in a hydroalcohol medium at a temperature of –5° C. at reflux, preferably at a temperature from +4° C. to +40° C. The compound (XI) is then obtained after acidification of the medium, preferably by a mineral acid such as hydrochloric acid.

The last coupling then occurs between the compound (XI) and the compound (V), the latter being optionally salified by a mineral or an organic acid.

The coupling methods are selected amongst the previously mentioned ones. Preferably, the coupling occurs using phosphonium salts such as BOP or PyBOP or PyBROP or PyCloP or PyClU or using uronium salts such as HBPyU (=O-(benzotriazol-1-yl)-N,N,N',N'-bis(tetramethylene)uronium hexafluorophosphate), or HBTU (=O-(benzotriazol-1-yl)-N,N,N',N'-tetramethyluronium hexafluorophosphate) or HATU (=O-(7-azabenzotriazol-1-yl)-N—,N,N',N'-tetramethyluronium hexa-fluorophosphate). More preferably, the coupling occurs with BOP or HBTU. Such a coupling occurs in an aprotic dipolar solvent such as DMF or NMP, or in an aprotic solvent such as THF or dioxane. The reaction is conducted in a basic medium, the base being preferably an organic base such as triethylamine, ethyldiisopropylamine or butylamine for example, the temperature being preferably set between –10° C. and 40° C. The compound (XII) is thereby obtained.

Second Preferred Embodiment of Step b) of the Method (FIG. 3)

According to a second preferred embodiment of the method for synthesizing KPV tripeptide diamide derivates, the KP dipeptide has the carboxylic function of the proline residue which is protected by a P3 protective group, then, the $P_3$ protective group is removed before coupling of the proline with the valine compound (V), an then the P1 protective group is removed and the free NH2(α) function of the lysine residue is amidated. The second preferred embodiment of the method is illustrated in FIG. 3.

According to this second embodiment, the method for synthesizing KPV tripeptide diamide derivates, such as generally defined in the specification, is characterized in that the step b) comprises the following steps of:

b5) removing the group $P_3$ from the compound having formula (IV) wherein the $P_3$ group represents a protective group, so as to obtain the compound with the following formula (VII):

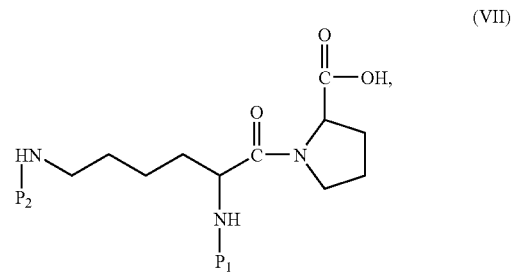

(VII)

wherein $P_1$ and $P_2$ have the same meanings as hereinabove;

b6) coupling the compound having the formula (VII) with the valine compound having the formula (V), optionally mineralized by an organic mineral acid:

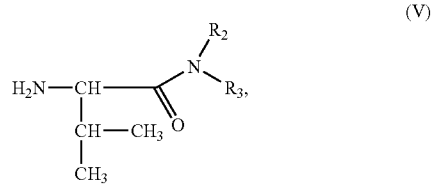

(V)

wherein $R_2$ and $R_3$ have the same meanings as hereinabove so as to obtain a compound of the formula (XIII):

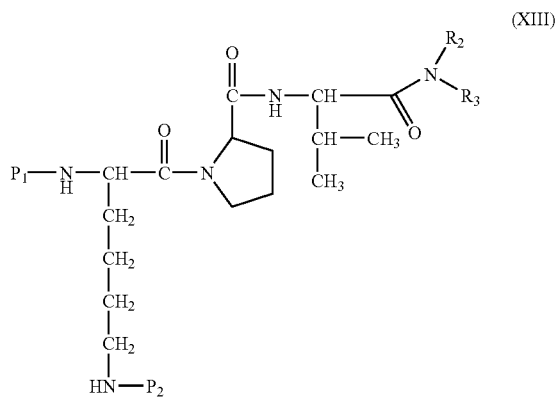

(XIII)

wherein $P_1$, $P_2$, $R_2$ and $R_3$ have the same meanings as hereinabove;

b7) removing the $P_1$ protective group from the compound having the formula (XIII) so as to obtain the following compound having the formula (XIV), and optionally salified by a mineral or an organic acid:

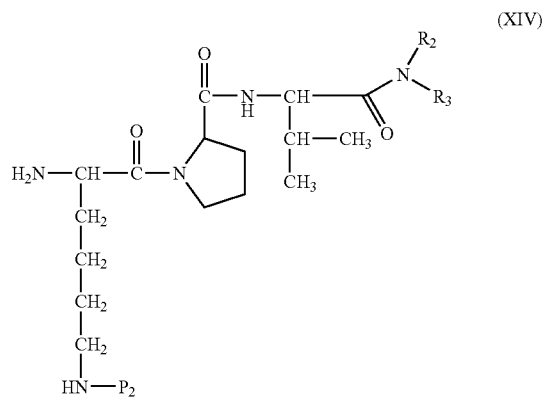

(XIV)

wherein $P_2$, $R_2$ and $R_3$ have the same meanings as hereinabove;

b8) amidating the $NH_2(\alpha)$ group of the lysine residue of the compound having the formula (XIV) with the compound having the formula (VI-A) or the following compound having the formula (VI-B), optionally salified by a mineral or an organic acid:

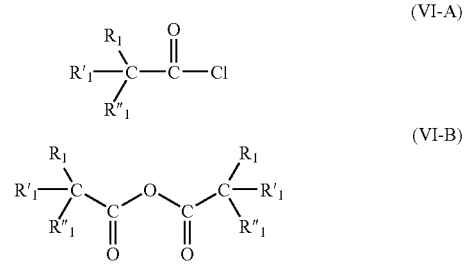

(VI-A)

(VI-B)

wherein $R_1$, $R'_1$ et $R''_1$ have the same meanings as hereinabove so as to obtain the following compound having the formula (XII):

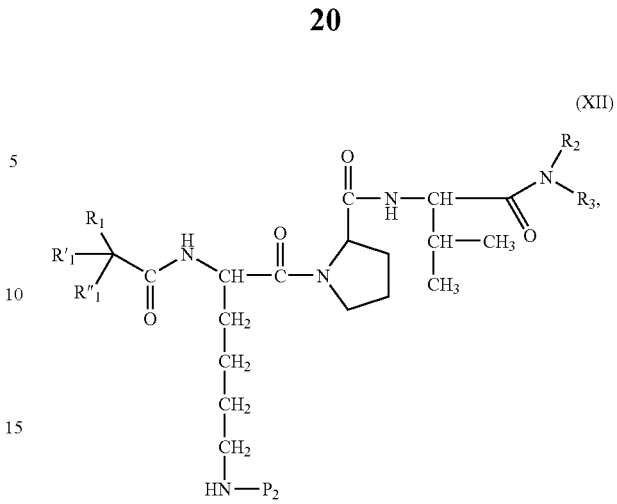

(XII)

wherein $P_2$, $R_1$, $R'_1$, $R''_1$, $R_2$ and $R_3$ have the same meanings as hereinabove.

According to the method illustrated in FIG. 3, the protected dipeptide (IV) is first saponified by a mineral base such as soda so as to obtain the derivate (VII). The peptide coupling between (VII) and the valine derivate (V) (or a salt thereof) occurs using one of the previously described methods, preferably using a method implementing carbodiimides. More preferably, the carbodiimide to be used is EDC. The reaction is then conducted in an aprotic dipolar solvent such as DMF or NMP or an aprotic solvent such as THF or dioxane, in a basic medium, for example through addition of an organic base such as triethylamine or ethyldiisopropylamine. The $N(\alpha)$ amine function of the thus obtained tripeptide (XIII) can then be released in an acidic medium, for example hydrochloric acid. Such a deprotection occurs for example by aqueous HCl in a dioxane-dichloromethane blend. The compound (XIV) is then obtained under a hydrochloride form. The salified $N(\alpha)$ amine function can be amidated for example through reaction with a symmetric anhydride (VI-B) in a basic medium such as in the presence of ethyldiisopropylamine or triethylamine, in an aprotic dipolar solvent such as DMF or NMP, preferably DMF, to lead to the tripeptide (XII).

Figure 4:
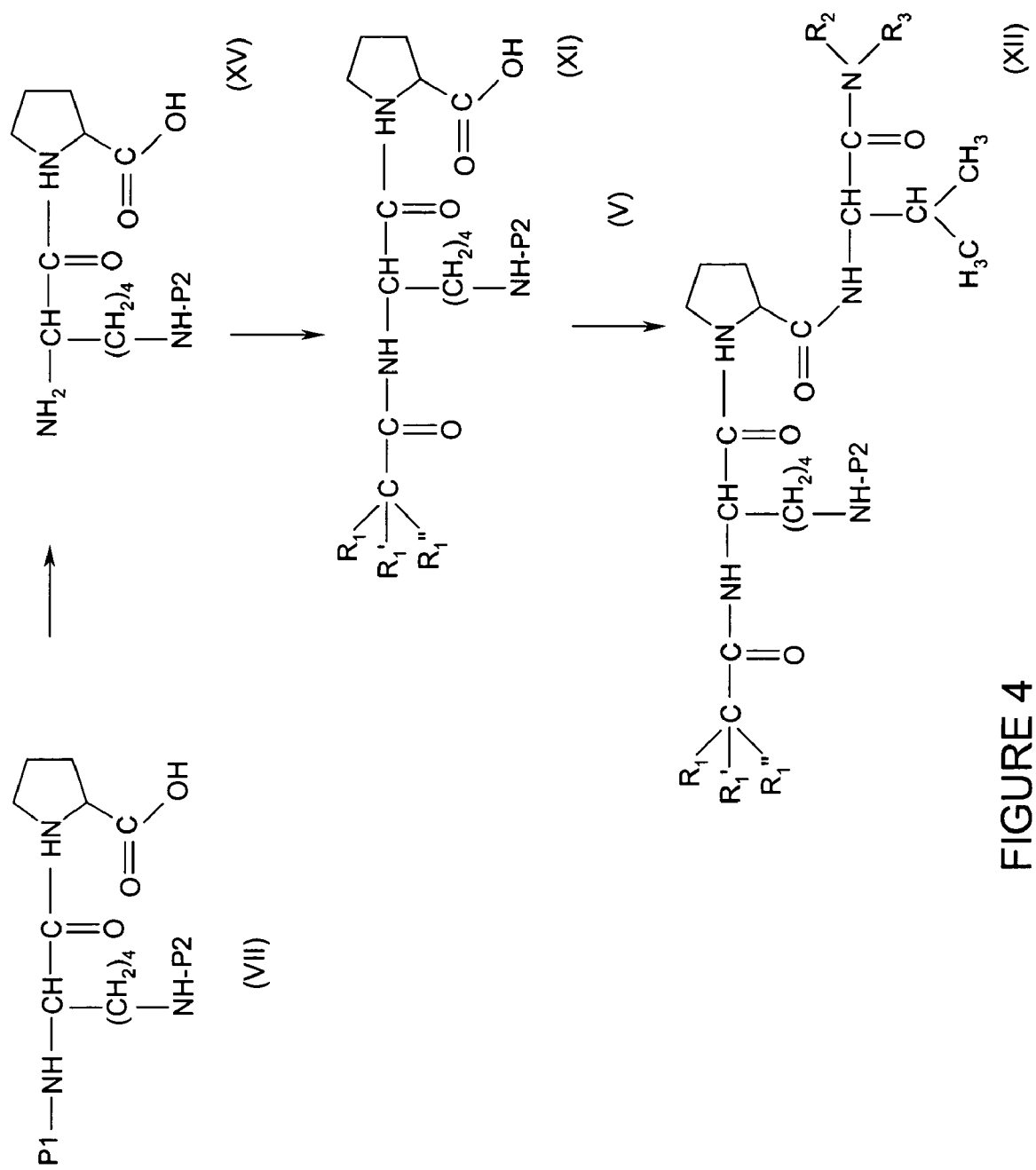
FIG. 4 illustrates the third preferred embodiment of the step b) of the method according to the invention.

Third preferred embodiment of step b) of the method
(FIG. 4)

According to a Third Preferred Embodiment of the Method, the KP Dipeptide

KP (XII) the carboxylic function of the proline residue of which is not protected ($P_3$=OH), the $P_1$ protective group is removed and the $NH2(\alpha)$ group of the lysine is amidated before coupling the resulting compound with the valine (III) residue. Said third embodiment of the method of the invention is illustrated in FIG. 4.

In this third preferred embodiment, the method for synthesizing KPV tripeptide diamide derivates, such as generally defined in the specification, is characterized in that the step b) comprises the following steps of:

b9) removing the $P_1$ protective group from the compound having the formula (VII) so as to obtain the following compound having the formula (XV), optionally salified by an organic or a mineral base:

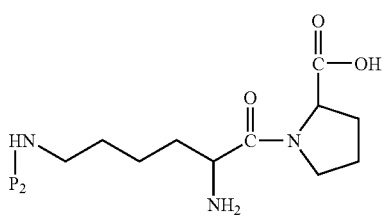
(XV)

wherein P₂ has the same meaning as hereinabove;

b10) amidating the $NH_2(\alpha)$ group of the lysine residue of the compound having the formula (XV) with the compound having the formula (VI-A) or the following compound having the formula (VI-B):

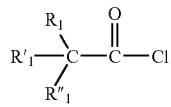
(VI-A)

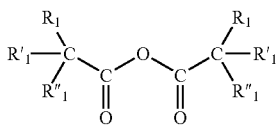
(VI-B)

wherein $R_1$, $R'_1$ et $R''_1$ have the same meanings as hereinabove;

so as to obtain the following compound (XI), optionally salified by an organic or a mineral base:

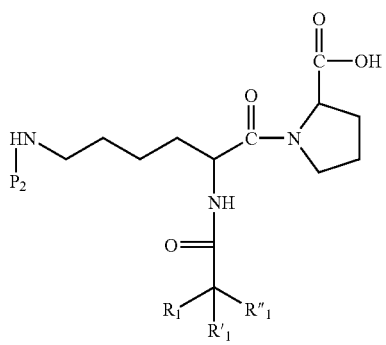
(XI)

wherein $P_2$, $R_1$, $R'_1$ et $R''_1$ have the same meanings as hereinabove;

b11) coupling the compound having the formula (XI) with the valine following compound having the formula (V), optionally salified by a mineral or an organic acid:

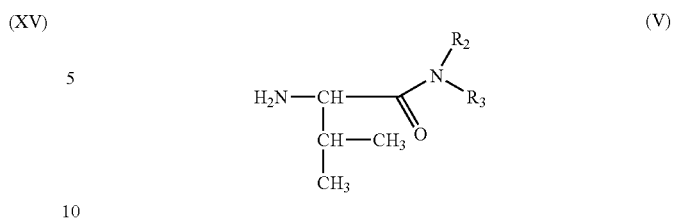
(V)

wherein $R_2$ et $R_3$ have the same meaning as hereinabove; so as to obtain the compound of formula (XII):

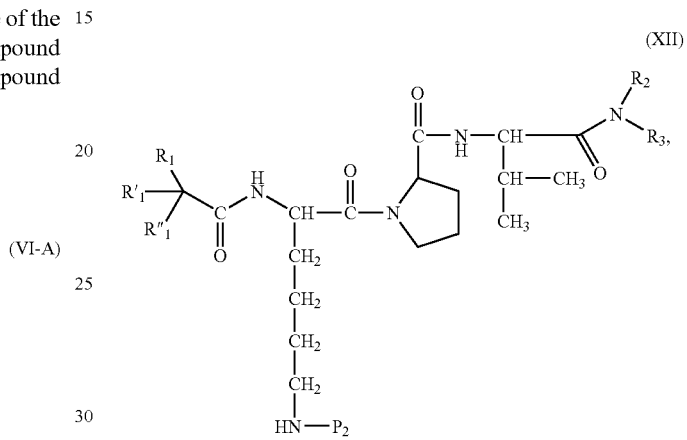
(XII)

wherein $P_2$, $R_1$, $R'_1$, $R''_1$, $R_2$ and $R_3$ have the same meanings as hereinabove.

According to the method illustrated in FIG. 4, the $N(\alpha)$ amine function of the derivate (VII) is released in an acidic medium, for example by hydrochloric acid. Such a deprotection is performed for example by an aqueous HCl in a dioxane-dichloromethane blend to lead to the salified compound (XV). The $N(\alpha)$ amine function can then be amidated as in FIG. 3 to lead to the derivate (XI).

The peptide coupling of (XI) with the valine derivate (V) (or a salt thereof) is performed by one of the previously described methods, preferably using a method implementing phosphonium salts. More preferably, the selected phosphonium salt is BOP. The reaction is conducted in an aprotic dipolar solvent such as DMF or NMP or in an aprotic solvent such as THF or dioxane, in a basic medium, for example through the addition of an organic base such as triethylamine or ethyl-diisopropylamine.

Preferred Embodiment of step c) of the Method

In step c) of the method, the P2 protective compound is removed from the compound having the formula (XII) so as to obtain the diamide derivate derivatized from the KPV having the formula (I), optionally under the form of a salt. Step c) of the method is illustrated in FIG. 5.

Figure 5:
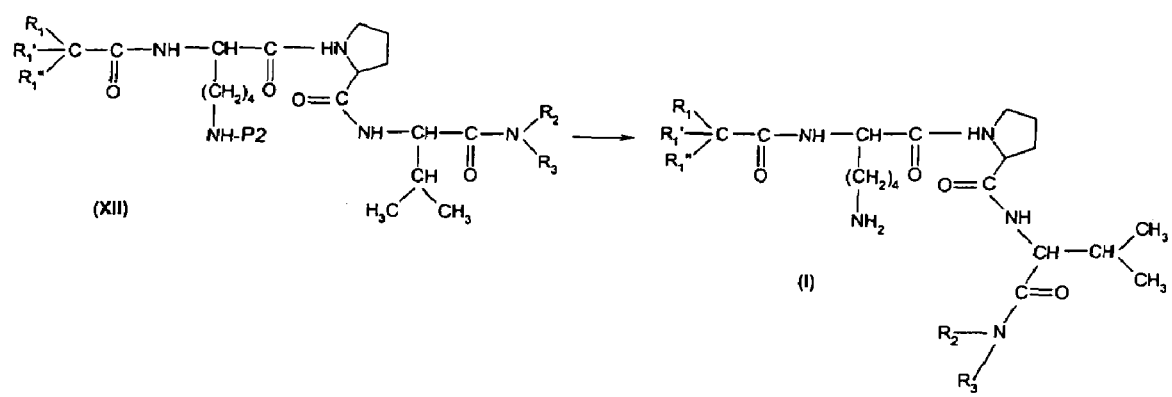
FIG. 5 illustrates the step c) of the method according to the invention.

The compound (XII) obtained according to any of the embodiments illustrated in FIGS. 2, 3 or 4, can then be easily transformed in one step to lead to the corresponding compound (I), said step being the deprotection of the $N(\epsilon)$ amine function of the lysine, as illustrated in FIG. 5.

Preferably, the $N(\epsilon)$ amine function is protected by a benzyloxycarbonyl (Z) group and the deprotection is conducted through a hydrogenation catalyzed by palladium on coal.

More preferably, the reaction is conducted under a hydrogen pressure ranging from 1 to 3 bars in an alcohol medium such as ethanol and in the presence of 1 to 5 equivalents of an organic acid such hydrochloric acid, hydrobromic acid, sulphuric acid, acetic acid, citric acid, tartaric acid, lactic acid, phosphoric acid, hydrogenophosphoric acid, propionic acid or succinic acid.

The hydrogenation preferably occurs between 5° C. and 50° C., more preferably between 10° C. and 30° C. The compound (I) is then directly obtained under a salified form.

Preferred General Technical Features of the Method

Preferably, the method according to the invention is characterized in that in the compound having the formula (II), the $P_1$ protective group is t-butyloxycarbonyl (Boc) and the $P_2$ protective group is benzyloxycarbonyl (Z).

Preferably, the method according to the invention is characterized in that in the compound having the formula (III), the $P_3$ protective group is the benzyl ester OBzl group.

Preferably, the method according to the invention is characterized in that in the compound having the formula (I), the $R_1$, $R'_1$ and $R''_1$ groups represent each a hydrogen atom.

Preferably, the method according to the invention is characterized in that in the compound having the formula (I), the $R_2$ et $R_3$ groups represent each a hydrogen atom.

Preferably, the method according to the invention is characterized in that the $P_1$ protective group is t-butyloxycarbonyl (Boc), the $P_2$ protective group is benzyloxycarbonyl (Z) and the $P_3$ protective group is the benzyl ester OBzl.

Best Embodiment of the Method According to the Invention

Most preferably, the diamides derived from the KPV tripeptide having the formula (I) are preferably obtained from the compound (II) wherein $P_1$ represents the t-butyloxycarbonyl group (Boc), and $P_2$ represents the benzyloxycarbonyl group (Z) and from the compound (III-A) wherein the acidic function is protected by a benzyl ester, the corresponding compound (III-A) being mineralized preferably by p-toluenesulfonic acid.

Such compounds are preferably implemented depending on the sequence of the routes as successively illustrated in FIG. 1A, then FIG. 2 (first preferred embodiment of step b) of the method), then FIG. 5, in order to obtain the KPV tripeptide diamide derivate having the formula (I).

Depending on the nature of the $R_1$, $R_1'$, $R_1''$, $R_2$ and $R_3$ substituents, the preferred sequence of the routes can allow for an implementation which does not require isolating and/or purifying the intermediate compounds. Thus for $R_1$, $R_1'$, $R_1''$, $R_2$ and $R_3$=H, the most preferred method implements the reagents and the operating conditions such as described in FIG. 6

Figure 6:
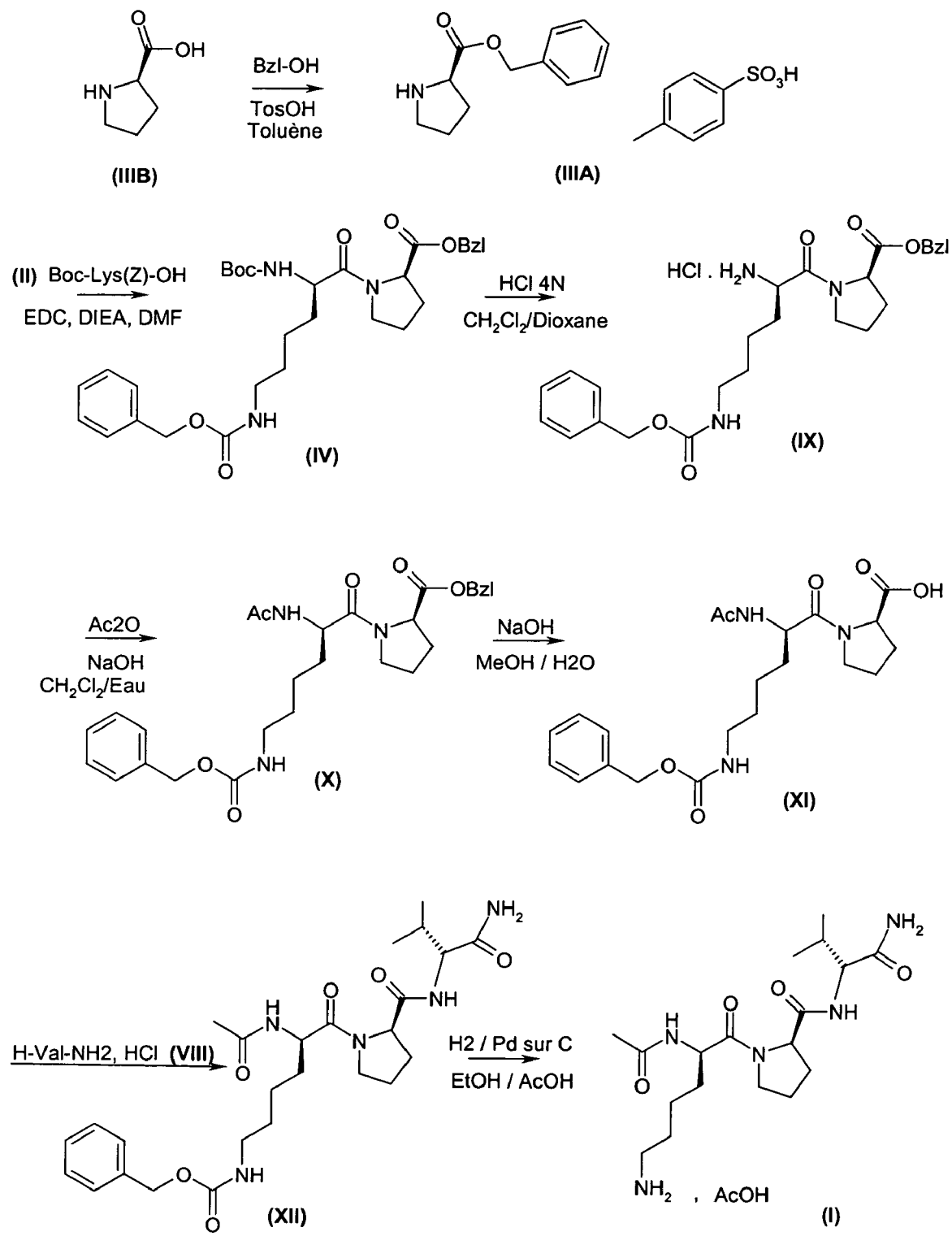
FIG. 6 represents the full reaction scheme of the best embodiment of the synthesis method of the KPV tripeptide diamide derivates according to the invention.

According to the embodiment of the method for synthesizing KPV tripeptide diamide derivates illustrated in FIG. 6, the intermediate compounds (III), (IV) and (IX) are not purified and are involved such as in the following steps. Such a method does not implement any chromatographic column purification or ion exchange. It is applicable to all the claimed salts. The purity of the final product is measured through HPLC.

More advantageously, the operating conditions minimize the racemization.

New Compounds and New Compositions According to the Invention

Another object of the invention is a diamide derivate or derivate salt of the KPV tripeptide having the following formula (IA):

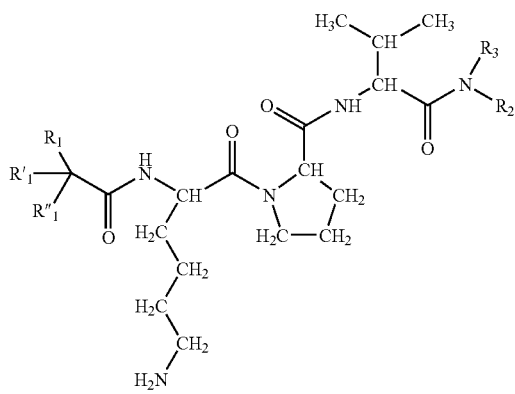

wherein:
a) $R_1$, $R'_1$ and $R''_1$ represent, independently from each other:
   a linear or branched $C_1$-$C_{22}$ alkyl moiety, optionally interrupted by a heteroatom such as O or N or S or Si,
   a $C_4$-$C_{10}$ cycloalkyl moiety,
   a linear or branched $C_1$-$C_{22}$ polyfluoroalkyl or perfluoroalkyl moiety,
   an aryl moiety optionally substituted by one or more halogen atoms such as Cl, F, Br or I, or one or more linear or branched $C_1$-$C_4$ alkyls,
   an aralkyl moiety,
   or $R_1$ and $R'_1$ could form with $C(R''_1)$ a saturated ring with from 3 to 7 atoms, optionally substituted by one or more linear or branched $C_1$-$C_4$ alkyl moieties and/or optionally containing a heteroatom such as O, S or N,
   hydrogen with the proviso that the $R_1(R'_1)(R''_1)CO$ group does not represent an amino acid residue or a peptide residue with at least one of R1, R'1, R"1 being different from hydrogen;

b) $R_2$ and $R_3$ represent, independently from each other, a hydrogen atom or represent:
   a linear or branched $C_1$-$C_{24}$ alkyl moiety, optionally interrupted by a heteroatom such as O or N or S or Si,
   a $C_4$-$C_{10}$ cycloalkyl moiety,
   a linear or branched $C_1$-$C_{22}$ polyfluoroalkyl or perfluoroalkyl moiety,
   an aryl moiety optionally substituted by one or more halogen atoms such as Cl, F, Br or I, or one or more linear or branched $C_1$-$C_4$ alkyl groups.
   an aralkyl moiety,
   or $R_2$ and $R_3$ could form with the nitrogen atom a saturated ring with 5 or 6 atoms optionally substituted by one or more linear or branched $C_1$-$C_4$ alkyl moieties, said saturated ring optionally containing a heteroatom such as O, S or also an additional nitrogen atom, with at least one of the R2 or R3 residues being different from hydrogen with the proviso that the $N(R_2)(R_3)$ group does not represent an amino acid or a peptide residue.

Preferably, the salt of the above-mentioned KPV tripeptide diamide derivate is selected amongst hydrochlorides, hydrobromides, sulfates, acetates, citrates, tartrates, lactates, phosphates, hydrogenophosphates, propionates and succinates.

Preferably the above-mentioned KPV tripeptide diamide derivate salt is characterized in that the Lysine, Proline or Valine amino acid residues could be any of the stereoisomers of each of such residues.

The invention is also relative to compositions containing, in a physiologically acceptable medium, a KPV tripeptide diamide derivate having the formula (IA) such as hereinabove defined.

According to a first advantageous embodiment, the above-mentioned compositions are characterized in that the medium is a cosmetic medium and in that the derivate (IA) is present in a content ranging from $10^{-8}$ to $10^{-3}$ g/100 g.

According to a second advantageous embodiment, the above-mentioned compositions are characterized in that the medium is a pharmaceutical medium and in that the derivate (IA) is present in a content higher than $5.10^4$ g/100 g.

The present invention also relates to using a derivate (IA) such as hereinabove defined in a cosmetic composition or for producing a dermatological composition for or designed for treating dry skins and/or sensitive skins.

The present invention is further illustrated, without any limitation, by the following example.

EXAMPLE

Synthesis of the KPV Tripeptide Diacetyl Derivate under the form of Various Salts

I. Preparation of TosOH, H-Pro-OBzl (III)

In an inert stirrable thermostable reactor provided with a Dean-Stark, 50.22 g of p-toluenesulfonic acid monohydrate (1.1 eq) and 140 ml of toluene are introduced at 20° C. The medium is stirred until dissolution and 74.5 ml of benzyl alcohol (3 eq) are added followed by 27.63 g of H-D-Pro-OH (240 mmoles). The blend is refluxed for 16 hours under a 250-300 mbar vacuum. The reaction completion is CCM controlled. The medium is vacuum concentrated until refusal.

The thus obtained product is used as such without any purification.

II. Preparation of Boc-D-Lys(Z)-D-Pro-OBzl (IV)

The residue from the previous step is recovered by 83 ml of DMF, added with 87 g of Boc-D-Lys(Z)-OH (1 eq), followed by 35 g of HOBt, 1 H$_2$O (1 eq). The blend is cooled down at 10° C. and, while maintaining such a temperature, 54.77 g of EDC are added (286 mmoles, 1.25 eq) followed by 59 ml of ethyldiisopropylamine (342.96 mmoles, 1.5 eq). The temperature is then allowed to reach 20° C. and then the solution is stirred for 2 to 20 hours.

The reaction completion is CCM controlled.

The reaction medium is poured onto 110 ml of dichloromethane and 220 ml water, stirred for 15 minutes, decanted and the organic phase is washed again with 2×220 ml of an NaHCO$_3$ saturated aqueous solution. The aqueous phases are extracted again in cascade with 83 ml of dichloromethane. The organic phases are gathered, dried on Na$_2$SO$_4$ and adjusted to 460 ml (by concentration or dilution).

Such a Boc-D-Lys(Z)-D-Pro-OBzl solution is used as such in the following step.

III. Preparation of HCl, H-D-Lys(Z)-D-Pro-OBzl (IX)

To the previous solution cooled down to 5° C. under inerting atmosphere, are added 460 ml (17 vol.) of 4N HCl in dioxane (1828 mmol, 8 eq). After returning to room temperature, stirring continues for 2 to 3 hours.

The reaction completion is CCM controlled.

The reaction medium is then poured under stirring onto a blend of 270 ml of water and 270 g of ice. The blend is decanted and the organic phase is used as such for the following step.

IV. Preparation of Ac-D-Lys(Z)-D-Pro-OBzl (X)

The previously obtained chloromethylene solution of HCl, H-D-Lys(Z)-D-Pro-OBzl is cooled down to 5° C., added with 135 ml of water, followed by 32.3 ml of acetic anhydride (1.5 eq). At Qsp pH 10 is then added within 30 minutes to 1 hour an aqueous 5N NaOH (90 to 130 ml are required).

The medium is stirred under room temperature for 2 h30 to 3 h, and the reaction completion is CCM controlled.

The medium is decanted, the organic phase is washed with water followed by a NaCl saturated aqueous solution (110 ml, 4 vol. each time). The organic phase is dried on Na$_2$SO$_4$ and vacuum concentrated (40° C. max, 50 mbar max.).

The residue is used as such in the subsequent step.

V. Preparation of Ac-D-Lys(Z)-D-Pro-OH (XI)

The Ac-D-Lys(Z)-D-Pro-OBzl compound obtained at the previous steps (in theory: 230 mmol) is mixed with 313 ml of methanol, added with 313 ml of 1N NaOH (313 mmol, 1.36 eq), and stirred overnight at room temperature. The reaction completion is CCM controlled. Thereafter, diisopropyl ether is added (313 ml, 11 vol.), the medium is decanted and the aqueous phase is extracted again three times with 3×150 ml of diisopropyl ether. The aqueous phase is then poured onto a blend of 540 ml of dichloromethane and 70 ml of aqueous 4N HCl (1.2 eq). The blend is stirred for 15 minutes and decanted. The separated organic phase is washed with water followed by a NaCl saturated aqueous solution (110 ml, 4 vol. each time). The organic phase is dried on Na$_2$SO$_4$ and vacuum concentrated (40° C. max, 50 mbar max.). The thus obtained product 94.25 g has the form of a foam (yield=98% calculated based on the involved Boc-D-Lys(Z)-OH).

VI. Preparation of Ac-D-Lys(Z)-D-Pro-D-Val-NH2 (XII)

In an inert thermostable reactor provided with a mechanical stirrer, 94.25 g of Ac-D-Lys(Z)-D-Pro-OH (XI) (224.7 mmol) are introduced followed by 470 ml of DMF. 32.58 g of HCl. H-D-Val-NH2 (V) (213.5 mmol, 0.95 eq) and 85.22 g of HBTU (1 eq) are then added. The medium is cooled down to 5° C., and 96.6 ml of ethyldiisopropylamine (2.5 eq) are added dropwise within 15 minutes. This is allowed to reach 0° C. again and after 1.30 to 2 hours, a strong crystallization could be observed. The reaction completion is CCM controlled. The reaction medium is then poured onto 2350 ml of AcOEt, stirred for 15 minutes, filtered and washed successively with 470 ml of AcOEt and 470 ml of diisopropyl ether. The derivate (XII) is vacuum dried at 25° C. This way, 107.2 g (92%) pf Ac-D-Lys(Z)-D-Pro-D-Val-NH2 are obtained.

VII. Preparation of AcOH, Ac-D-Lys-D-Pro-D-Val-NH2 (1)

The last step comprises hydrogenolyzing the Z benzyloxycarbonyl protective group of the lysine. The acid used in the reaction medium is caused to salify the released amine function.

1) Isolated under the Acetate Form 107 g of Ac-D-Lys(Z)-D-Pro-D-Val-NH2 are dissolved in 535 ml of EtOH, added with 214 ml of AcOH and of 21.4 g of Pd/C at 10% at 50% water. The hydrogenation is conducted at 20° C., under a 1 bar hydrogen pressure for 16 hours. The reaction completion is CCM controlled. The catalyst is filtered and the filtrate is vacuum concentrated until refusal. The residue is recovered with 107 ml of EtOH, added with 430 ml of iPrOH and the blend is heated at 50° C., then added dropwise at 50° C. with 1500 ml of diisopropyl ether. The expected product crystallizes. The medium is cooled down to 20° C. and stirred for 1 hour. The solid is filtered and washed with 500 ml of diisopropyl ether before being vacuum dried at 25° C. so to provide 78.3 g of Ac-D-Lys-D-Pro-D-Val-NH2 under the form of an acetate salt (yield 85.4%). The thus obtained product purity is HPLC controlled.

If required, the product is "recrystallized" with a 0.5μ filtration, in the same conditions so as to provide 71 g of AcOH. Ac-D-Lys-D-Pro-D-Val-NH2 (purification yield=91%; overall yield 74% based on Boc-D-Lys(Z)-OH).

2) Isolated under the Tartrate Form

The tartrate is obtained conducting the hydrogenolysis of the Z benzyloxycarbonyl group in the presence of tartaric acid. The L acid and the D-tartaric acid both provide a comparable salt.

5 g of Ac-D-Lys(Z)-D-Pro-D-Val-NH2 are suspended in 25 ml of EtOH, added with 1.48 g of L-(+)-tartaric acid (1.02 eq.) and 0.5 g of Pd/C at 10% at 50% of water. The hydrogenation is conducted at 20° C., under a 1 bar hydrogen pressure, for 16 hours.

The reaction completion is CCM controlled. The product has partially crystallized in the medium. 10 ml of water are then added, the catalyst is filtered and the filtrate is vacuum concentrated until refusal. The residue is recovered with 40 ml of iPrOH heated at 50° C. and added at 50° C. with dropwise introduced 40 ml of ethanol. The product crystallizes. The medium is cooled down at 20° C. and stirred for 1 hour before being added with 40 ml of iPrOH and 50 ml of diisopropyl ether. The expected solid is filtered and washed with 50 ml of diisopropyl ether before being vacuum dried at 25° C. so as to provided 4.12 g of tartrate. Ac-D-Lys-D-Pro-D-Val-NH2 (yield 80%). The thus obtained product is HPLC controlled. If required, it can be purified as follows.

The obtained product is dissolved in 2 volumes of ethanol and 1 volume of water, filtered and added with 4 volumes of isopropanol. The solution is filtered then added with 14 volumes of filtered diisopropyl ether. After the formed crystals have been spin-dried and dried at 20° C. under vacuum, 90% of recrystallized filtered product is obtained.

3) Isolated under the Succinate or Citrate Form

The protocol described with the tartaric acid can be reproduced with succinic acid or citric acid.

If required, the product can be purified with a 0.5μ filtration dissolving the respective salts in 2 volumes of ethanol added with one volume of water, followed by the addition of 4 filtered volumes of isopropanol and 14 filtered volumes of diisopropyl ether.

REFERENCES

A. EBERLE, J. L. FAUCHERE, G. I. TESSER, R. SCHWYZER, *Helvetica Chimica Acta*, 1975, Vol 58, 2106.
SULI-VARGHA H., JENEY A., LAPIS K., MEDZIHRADSZKY K., *J. Med. Chem.*, 1987, 30(3), 583-6.
SULI-VARGHA H., MEDZIHRADSZKY K, *Int. J. Pept. Protein Res.*, 1984, 23 (6), 650-6.
YASUTAKE A., POWERS J., *Biochemistry*, 1981, 20 (13), 3675-9.
R. SCHWYZER, A. COSTOPANAGIOTIS, P. SIEBER, *Helv. Chim. Acta*, 1963, 46, 870-889.
K. HOFMANN, M. WOOLNER, H. YAJIMA, G. SPUHLER, T. THOMPSON, E. SCHWARTZ, *J. Am. Chem. Soc.*, 1958, 80, 6458
K. HOFFMANN, T. THOMPSON, M. WOOLNER, G. SPUHLER, H. YAJIMA, J. CIPERA, E. SCHWARTZ, *J. Am. Chem. Soc.*, 1960, 3721.
STAPLES D., SAWYER T., MAC HADLEY E., ENGEL M., DEVAUX A., AFFHOLTER J., DARMAN P., CODY W., WILKES B., HRUBY, V., Pept.: Struct. Funct., *Proc. Am. Pept. Symp.*, 9th (1985), 6914.
T. SAWYER, V. HRUBY, B. WILKES, M. DRAELOS, E. Mac HADLEY, M. BERGSNEIDER, *J. Med. Chem.*, 1982, 25, 1022-1027.
T. SAWYER, Thesis, University of Arizona, 1981

The invention claimed is:

1. A method for the synthesis of a KPV tripeptide diamide derivative represented by the following formula (I)

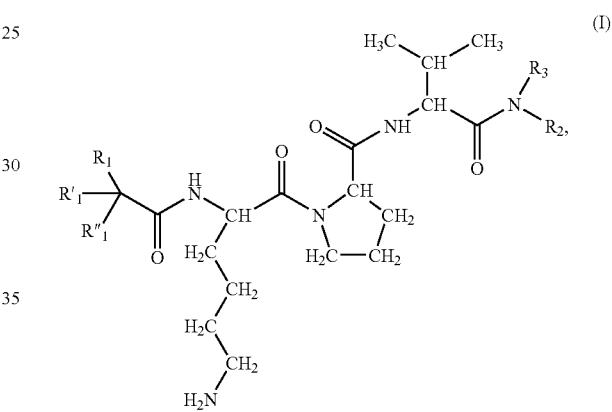

or for a salt thereof, independent of stereochemistry wherein:

a) $R_1$, $R'_1$ and $R''_1$ represent, independently from each other, a hydrogen atom or a linear or branched $C_1$-$C_{22}$ alkyl moiety, optionally interrupted by a heteroatom, $C_4$-$C_{10}$ cycloalkyl moiety, a linear or branched $C_1$-$C_{22}$ polyfluoroalkyl or perfluoroalkyl moiety, an aryl moiety optionally substituted by one or more halogen atoms or more linear or branched $C_1$-$C_4$ alkyl moieties, an aralkyl moiety, or $R_1$ and $R'_1$ could form with $C(R''_1)$ a saturated ring with from 3 to 7 atoms, optionally substituted by one or more linear or branched $C_1$-$C_4$ alkyl moieties and/or optionally containing a heteroatom, with the proviso that the $R_1(R'_1)$ $(R''_1)CO$ group does not represent an amino acid residue or a peptide;

b) $R_2$ and $R_3$ represent, independently from each other, a hydrogen atom or represent a linear or branched $C_1$-$C_{24}$ alkyl moiety, optionally interrupted by a heteroatom, a $C_4$-$C_{10}$ cycloalkyl moiety, a linear or branched $C_1$-$C_{22}$ polyfluoroalkyl or perfluoroalkyl moiety, an aryl moiety optionally substituted by one or more halogen atoms or one or more linear or branched $C_1$-$C_4$ alkyl moieties, an aralkyl moiety, or $R_2$ and $R_3$ could form with the nitrogen atom a saturated ring with from 5 or 6 atoms optionally substituted by one or more linear or branched $C_1$-$C_4$ alkyl moieties, said saturated ring optionally containing a heteroatom with the proviso that the $N(R_2)$ $(R_3)$ group does not represent an amino acid or a peptide;

said method comprising:

a) reacting a lysine diprotected residue having the following formula (II):

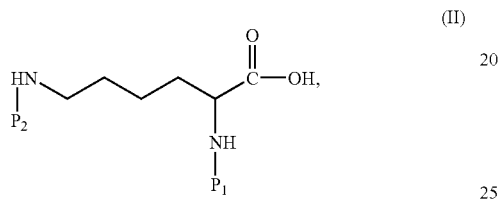
(II)

optionally salified by a mineral or organic base, wherein $P_1$ and $P_2$, are different and each represent independently from one another a protective group, with a proline residue having the following formula (III):

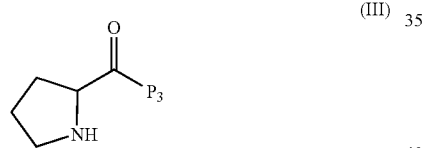
(III)

optionally salified by a mineral or organic acid, wherein $P_3$ represents a protective group differing from any of the $P_1$ and $P_2$ protective groups, in the presence of an activation reagent or a coupling reagent and in a solvent, so as to obtain the following compound having the formula (IV):

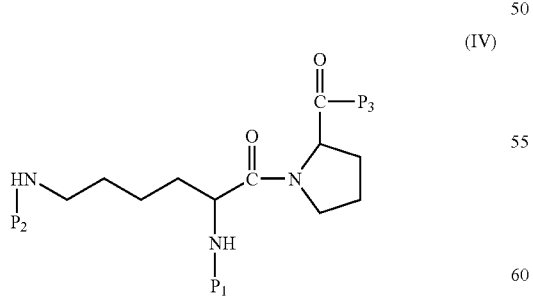
(IV)

wherein $P_1$, $P_2$ and $P_3$ have the abovementioned meanings, b)

1) removing the P1 protective group of the compound of formula (IV) to obtain the compound of formula (IX):

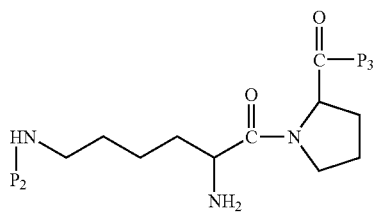
(IX)

2) amidating a $NH_2(\alpha)$ group of the lysine residue of the compound of the formula (IX) with a compound having formula (VI-A) or a compound having formula (VI-B) to obtain the compound of formula (X):

(VI-A)

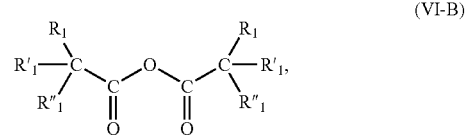
(VI-B)

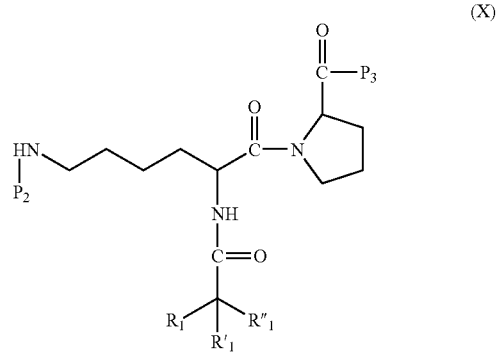
(X)

3) removing the $P_3$ protective group from the compound of formula (X) to obtain the compound of formula (XI):

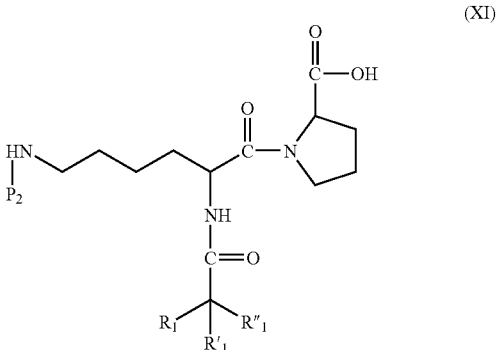
(XI)

4) coupling the compound of formula (XI) with the valine compound of formula (V), or the mineral or organic salt thereof, to form the compound of formula (XII):

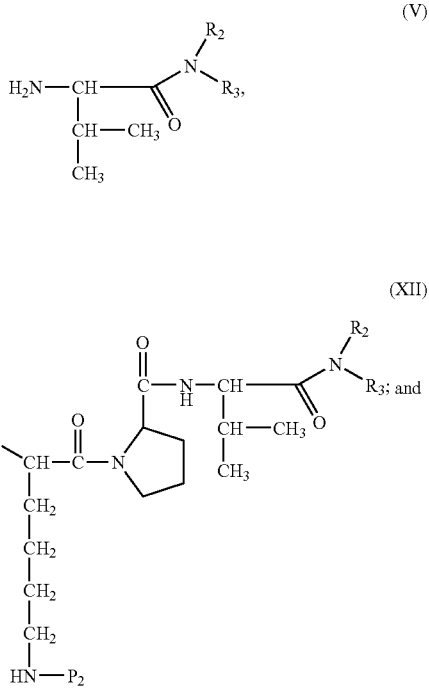

c) removing the $P_2$ protective group from the compound of formula (XII) to obtain the compound of the formula (I) or the mineral or organic salt thereof.

2. The method according to claim 1, wherein the compound having the formula (I) is a salt selected amongst the hydrochlorides, hydrobromides, sulphates, acetates, citrates, tartrates, lactates, phosphates, hydrogenophosphates, propionates and succinates.

3. The method according to claims 1 or 2, wherein the lysine, proline or valine amino acid residues are any of the stereoisomers of such residues.

4. The method according to claims 1 or 2, wherein the salt is obtained during step c) through introducing the corresponding acid.

5. The method according to claim 4, wherein the acid is acetic acid, hydrochloric acid, hydrobromic acid, sulphuric acid, citric acid, tartaric acid, lactic acid, phosphoric acid, hydrogenophosphoric acid, propionic acid or succinic acid.

6. The method according to claim 5, wherein the acid is acetic or hydrochloric acid.

7. The method according to claims 1 or 2, wherein the $P_1$ and $P_2$ protective groups represent, independently from each other, Adoc (1-adamantyloxycarbonyl) BOC (t-butyloxycarbonyl), 2-bromo-Z (2-bromo-benzyloxycarbonyl), 2-chloro-Z (2-chloro-benzyloxycarbonyl), Fmoc (9-fluorenylmethoxycarbonyl), Formyl, Nicotinoyl, 4-nitro-Z (4-nitro-benzyloxycarbonyl), Tfa (trifluoroacetyl), Tos (p-toluenesulfonyl), Z(benzyloxycarbonyl) or Adpoc (1-(adamantyl)-1methylethoxycarbonyl).

8. The method according to claims 1 or 2, wherein the $P_1$ and $P_2$ protective groups are selected such as to be removed respectively under distinct operating conditions.

9. The method according to claims 1 or 2, wherein the compound having the formula (II) is salified by an organic base.

10. The method according to claims 1 or 2, wherein the compound having the formula (III) is salified by a mineral or an organic acid.

11. A method according to claims 1 or 2, wherein in step a), the peptide coupling reaction occurs in the presence of an activation or a coupling reagent selected amongst carbodiimides, water-soluble carbodiimides, phosphonium salts, PyBOP ((benzotriazol-1-yloxy)tripyrrolidino-phosphonium hexafluorophosphate), PyBROP (bromotripyrrolidino-phosphonium hexafluorophosphate), PyCloP (chlorotripyrrolidino-phosphonium hexafluorophosphate), or also by means of reagents selected amongst PyClU (chloro-N,N,N',N'-bis(tetramethylene) formamidinium hexafluoro-phosphate), N-hydroxysuccinimide, EEDQ (1-ethoxycarbonyl-2-ethoxy1,2-dihydroquinolin), CDI (carbonyldiimidazole), or chloroformates.

12. The method according to claims 1 or 2, wherein in the compound having the formula (II), the $P_1$ protective group is t-butyloxycarbonyl (BOC) and the $P_2$ protective group is benzyloxycarbonyl (Z).

13. The method according to claims 1 or 2, wherein in the compound of the formula (III), the $P_3$ protective group is the OBzl ester group.

14. The method according to claims 1 or 2, wherein in the compound having the formula (I), the $R_1$, $R'_1$ and $R''_1$ groups represent each a hydrogen atom.

15. The method according to claims 1 or 2, wherein in the compound having the formula (I), the $R_2$ and $R_3$ groups represent each a hydrogen atom.

16. The method according to claims 1 or 2, wherein the $P_1$ protective group is t-butyloxycarbonyl (BOC), the $P_2$ protective group is benzyloxycarbonyl (Z) and the $P_3$ protective group is OBzl ester.

17. The method according to claim 9, wherein the organic base is an organic amine.

18. The method of claim 1, which does not comprise a final purification step.

* * * * *

UNITED STATES PATENT AND TRADEMARK OFFICE
CERTIFICATE OF CORRECTION

PATENT NO. : 7,683,026 B2  Page 1 of 1
APPLICATION NO. : 10/764158
DATED : March 23, 2010
INVENTOR(S) : Sylvie Genard It is certified that error appears in the above-identified patent and that said Letters Patent is hereby corrected as shown below:

Column 20, Lines 53 through 58 insert all text therein beginning with --KP (XII) and ending with the words in FIG. 4-- after KP Dipeptide in Line 52. (1 Paragraph)

Signed and Sealed this

Eighth Day of March, 2011

David J. Kappos
*Director of the United States Patent and Trademark Office*